(12) United States Patent
Blacklow et al.

(10) Patent No.: US 8,236,753 B2
(45) Date of Patent: Aug. 7, 2012

(54) RAP VARIANTS FOR DRUG DELIVERY AND METHODS OF USE THEREOF

(75) Inventors: Stephen Blacklow, Cambridge, MA (US); Carl Fisher, Watertown, MA (US); Kristine Estrada, Chino Hills, CA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 12/747,354

(22) PCT Filed: Dec. 10, 2008

(86) PCT No.: PCT/US2008/013542
§ 371 (c)(1),
(2), (4) Date: Oct. 18, 2010

(87) PCT Pub. No.: WO2009/075836
PCT Pub. Date: Jun. 18, 2009

(65) Prior Publication Data
US 2011/0028384 A1    Feb. 3, 2011

Related U.S. Application Data

(60) Provisional application No. 61/008,827, filed on Dec. 21, 2007, provisional application No. 61/007,124, filed on Dec. 10, 2007.

(51) Int. Cl.
| | |
|---|---|
| A61K 38/00 | (2006.01) |
| A61K 47/00 | (2006.01) |
| C07K 1/00 | (2006.01) |
| C07K 14/00 | (2006.01) |
| C07K 16/00 | (2006.01) |
| C07K 17/00 | (2006.01) |
| C08H 1/00 | (2006.01) |

(52) U.S. Cl. .................... 514/1.2; 530/350; 530/402
(58) Field of Classification Search ................ None
See application file for complete search history.

(56) References Cited

U.S. PATENT DOCUMENTS

| | | |
|---|---|---|
| 5,284,656 A | 2/1994 | Platz et al. |
| 5,451,569 A | 9/1995 | Wong et al. |
| 2005/0026823 A1 | 2/2005 | Zankel et al. |
| 2006/0029609 A1 | 2/2006 | Zankel et al. |

FOREIGN PATENT DOCUMENTS

| | | |
|---|---|---|
| WO | WO 2006/138343 A2 | 12/2006 |
| WO | WO 2007/035716 A2 | 3/2007 |

OTHER PUBLICATIONS

Genbank Submission; NIH/NCBI, Accession No. M63959; Striekland et al.; Oct. 30, 1994.
Adjei et al., Pulmonary delivery of peptide drugs: effect of particle size on bioavailability of leuprolide acetate in healthy male volunteers. Pharm Res. Jun. 1990;7(6):565-9.
Benoist et al., In vivo sequence requirements of the SV40 early promotor region. Nature. Mar. 26, 1981;290(5804):304-10.
Blacklow, Versatility in ligand recognition by LDL receptor family proteins: advances and frontiers. Curr Opin Struct Biol. Aug. 2007;17(4):419-26. Epub Sep. 17, 2007.
Bollon et al., DNA transformation efficiency of various bacterial and yeast host-vector systems. J Clin Hematol Oncol. 1980;10:39-48.
Broach, The yeast plasmid 2 mu circle. Cell. Feb. 1982;28(2):203-4.
Estrada et al., Unfolding of the RAP-D3 helical bundle facilitates dissociation of RAP-receptor complexes. Biochemistry. Feb. 12, 2008;47(6):1532-9. Epub Jan. 5, 2008.
Fisher et al., Structure of an LDLR-RAP complex reveals a general mode for ligand recognition by lipoprotein receptors. Mol Cell. Apr. 21, 2006;22(2):277-83.
Hamer et al., Regulation in vivo of a cloned mammalian gene: cadmium induces the transcription of a mouse metallothionein gene in SV40 vectors. J Mol Appl Genet. 1982;1(4):273-88.
Herz, LRP: a bright beacon at the blood-brain barrier. J Clin Invest. Nov. 2003;112(10):1483-5.
Howard et al., Identification of DNA repair and damage induced proteins from Neurospora crassa. Mol Gen Genet. Jun. 1986;203(3):462-7.
Isbell et al., Functional mimicry of the LDL receptor-associated protein through multimerization of a minimized third domain. Biochem Biophys Res Commun. Dec. 21, 2007;364(3):614-9. Epub Oct. 18, 2007.
Isbell et al., Minimization of the third domain of the LDL receptor-associated protein (RAP). Biochem Biophys Res Commun. Sep. 28, 2007;361(3):758-62. Epub Jul. 26, 2007.
Izaki, [Plasmid-determined resistance to heavy metals (author's transl)]. Nippon Saikingaku Zasshi. 1978;33(6):729-42. Japanese.
John et al., Plasmids as epidemiologic markers in nosocomial gram-negative bacilli: experience at a university and review of the literature. Rev Infect Dis. Sep.-Oct. 1986;8(5):693-704.
Johnston et al., Isolation of the yeast regulatory gene GAL4 and analysis of its dosage effects on the galactose/melibiose regulon. Proc Natl Acad Sci U S A. Nov. 1982;79(22):6971-5.
Kendall et al., Plasmid transfer in *Streptomyces lividans*: identification of a kil-kor system associated with the transfer region of pIJ101. J Bacteriol. Sep. 1987;169(9):4177-83.
Langer, New methods of drug delivery. Science. Sep. 28, 1990;249(4976):1527-33.
Lee et al., RAP uses a histidine switch to regulate its interaction with LRP in the ER and Golgi. Mol Cell. May 5, 2006;22(3):423-30.
Lee et al., The structure of receptor-associated protein (RAP). Protein Sci. Aug. 2007;16(8):1628-40.
Li et al., In vitro invasiveness of human breast cancer cells is promoted by low density lipoprotein receptor-related protein. Invasion Metastasis. 1998-1999;18(5-6):240-51.
McKnight, Functional relationships between transcriptional control signals of the thymidine kinase gene of herpes simplex virus. Cell. Dec. 1982;31(2 Pt 1):355-65.
Newmark et al., Preparation and Properties of Adducts of Streptokinase and Streptokinase-Plasmin Complex with Polyethylene Glycol and Pluronic Polyol F38. J Appl Biochem. 1982;4:185-189.

(Continued)

*Primary Examiner* — Robert Landsman
(74) *Attorney, Agent, or Firm* — Wolf, Greenfield & Sacks, P.C.

(57) ABSTRACT

The present invention relates to stabilized RAP variants and methods of use thereof. Conjugates of stabilized RAP variants to therapeutic compounds and stabilized RAP fusion proteins comprising therapeutic polypeptides are also presented.

16 Claims, 9 Drawing Sheets

OTHER PUBLICATIONS

Okayama et al., A cDNA cloning vector that permits expression of cDNA inserts in mammalian cells. Mol Cell Biol. Feb. 1983;3(2):280-9.

Pan et al., Efficient transfer of receptor-associated protein (RAP) across the blood-brain barrier. J Cell Sci. Oct. 1, 2004;117(Pt 21):5071-8. Epub Sep. 21, 2004.

Sawhney et al., Bioerodible Hydrogels Based on Photopolymerized Poly(ethylene glycol)-co-poly(α-hydroxyl acid) Diacrylate Macromers. Macromolecules. 1993;26:581-7.

Silver et al., Amino terminus of the yeast GAL4 gene product is sufficient for nuclear localization. Proc Natl Acad Sci U S A. Oct. 1984;81(19):5951-5.

Smith et al., Pulmonary deposition and clearance of aerosolized alpha-1-proteinase inhibitor administered to dogs and to sheep. J Clin Invest. Oct. 1989;84(4):1145-54.

Strickland et al., Primary Structure of $\alpha_2$-Macroglobulin Receptor-associated Protein. J Biol Chem. 1991;266:13364-13369.

Ulmanen et al., Transcription and translation of foreign genes in *Bacillus subtilis* by the aid of a secretion vector. J Bacteriol. Apr. 1985;162(1):176-82.

Veinbergs et al., Role of apolipoprotein E receptors in regulating the differential in vivo neurotrophic effects of apolipoprotein E. Exp Neurol. Jul. 2001;170(1):15-26.

Walensky et al., A stapled BID BH3 helix directly binds and activates BAX. Mol Cell. Oct. 20, 2006;24(2):199-210.

Ward et al., Construction and characterisation of a series of multi-copy promoter-probe plasmid vectors for *Streptomyces* using the aminoglycoside phosphotransferase gene from Tn5 as indicator. Mol Gen Genet. Jun. 1986;203(3):468-78.

Warshawsky et al., 39-kD protein inhibits tissue-type plasminogen activator clearance in vivo. J Clin Invest. Aug. 1993;92(2):937-44.

Westendorf et al., Wnt signaling in osteoblasts and bone diseases. Gene. Oct. 27, 2004;341:19-39.

Williams, Defining neurodegenerative diseases. BMJ. Jun. 22, 2002;324(7352):1465-6.

Yepes et al., Tissue-type plasminogen activator induces opening of the blood-brain barrier via the LDL receptor-related protein. J Clin Invest. Nov. 2003;112(10):1533-40.

8,236,753 B2

SEQUENCE LISTING

```
<160> NUMBER OF SEQ ID NOS: 4

<210> SEQ ID NO 1
<211> LENGTH: 115
<212> TYPE: PRT
<213> ORGANISM: homo sapiens

<400> SEQUENCE: 1

Glu Asn Leu Tyr Phe Gln Gly Ala Glu Phe Glu Pro Arg Val Ile
1               5                   10                  15

Asp Leu Trp Asp Leu Ala Gln Ser Ala Asn Leu Thr Asp Lys Glu Leu
            20                  25                  30

Glu Ala Phe Arg Glu Glu Leu Lys His Phe Glu Ala Lys Ile Glu Lys
        35                  40                  45

Phe Asn Phe Tyr Gln Lys Gln Leu Glu Ile Ala His Glu Lys Leu Arg
    50                  55                  60

His Ala Glu Ser Val Gly Asp Gly Glu Arg Val Ser Arg Ser Arg Glu
```

```
                65                  70                  75                  80
Lys His Ala Leu Leu Glu Gly Arg Thr Lys Glu Leu Gly Tyr Thr Val
                    85                  90                  95
Lys Lys His Leu Gln Asp Leu Ser Gly Arg Ile Ser Arg Ala Arg His
            100                 105                 110
Asn Glu Leu
        115

<210> SEQ ID NO 2
<211> LENGTH: 115
<212> TYPE: PRT
<213> ORGANISM: homo sapiens

<400> SEQUENCE: 2

Glu Asn Leu Tyr Phe Gln Gly Ala Glu Phe Glu Glu Pro Arg Val Ile
1               5                   10                  15
Asp Leu Trp Asp Leu Ala Gln Ser Ala Asn Leu Thr Asp Lys Glu Leu
            20                  25                  30
Glu Ala Phe Arg Glu Glu Leu Lys His Phe Glu Ala Lys Ile Glu Lys
        35                  40                  45
His Asn His Tyr Gln Lys Gln Leu Glu Ile Ala Phe Glu Lys Leu Arg
    50                  55                  60
His Ala Glu Ser Val Gly Asp Gly Glu Arg Val Ser Arg Ser Arg Glu
65                  70                  75                  80
Lys Phe Ala Leu Leu Glu Gly Arg Thr Lys Glu Leu Gly Tyr Thr Val
                85                  90                  95
Lys Lys His Leu Gln Asp Leu Ser Gly Arg Ile Ser Arg Ala Arg His
            100                 105                 110
Asn Glu Leu
        115

<210> SEQ ID NO 3
<211> LENGTH: 115
<212> TYPE: PRT
<213> ORGANISM: homo sapiens

<400> SEQUENCE: 3

Glu Asn Leu Tyr Phe Gln Gly Ala Glu Phe Glu Glu Pro Arg Val Ile
1               5                   10                  15
Asp Leu Trp Asp Leu Ala Gln Ser Ala Asn Leu Thr Asp Lys Glu Leu
            20                  25                  30
Glu Ala Phe Arg Glu Glu Leu Lys His Phe Glu Ala Lys Ile Glu Lys
        35                  40                  45
Phe Asn Phe Tyr Gln Lys Gln Leu Glu Ile Ala Phe Glu Lys Leu Arg
    50                  55                  60
His Ala Glu Ser Val Gly Asp Gly Glu Arg Val Ser Arg Ser Arg Glu
65                  70                  75                  80
Lys Phe Ala Leu Leu Glu Gly Arg Thr Lys Glu Leu Gly Tyr Thr Val
                85                  90                  95
Lys Lys His Leu Gln Asp Leu Ser Gly Arg Ile Ser Arg Ala Arg His
            100                 105                 110
Asn Glu Leu
        115

<210> SEQ ID NO 4
<211> LENGTH: 330
<212> TYPE: PRT
<213> ORGANISM: homo sapiens
```

```
<400> SEQUENCE: 4

Glu Asn Leu Tyr Phe Gln Gly Tyr Ser Arg Glu Lys Asn Gln Pro Lys
1               5                   10                  15

Pro Ser Pro Lys Arg Glu Ser Gly Glu Glu Phe Arg Met Glu Lys Leu
            20                  25                  30

Asn Gln Leu Trp Glu Lys Ala Gln Arg Leu His Leu Pro Pro Val Arg
            35                  40                  45

Leu Ala Glu Leu His Ala Asp Leu Lys Ile Gln Glu Arg Asp Glu Leu
        50                  55                  60

Ala Trp Lys Lys Leu Lys Leu Asp Gly Leu Asp Glu Asp Gly Glu Lys
65                  70                  75                  80

Glu Ala Arg Leu Ile Arg Asn Leu Asn Val Ile Leu Ala Lys Tyr Gly
                85                  90                  95

Leu Asp Gly Lys Lys Asp Ala Arg Gln Val Thr Ser Asn Ser Leu Ser
            100                 105                 110

Gly Thr Gln Glu Asp Gly Leu Asp Asp Pro Arg Leu Glu Lys Leu Trp
            115                 120                 125

His Lys Ala Lys Thr Ser Gly Lys Phe Ser Gly Glu Glu Leu Asp Lys
    130                 135                 140

Leu Trp Arg Glu Phe Leu His His Lys Glu Lys Val His Glu Tyr Asn
145                 150                 155                 160

Val Leu Leu Glu Thr Leu Ser Arg Thr Glu Glu Ile His Glu Asn Val
                165                 170                 175

Ile Ser Pro Ser Asp Leu Ser Asp Ile Lys Gly Ser Val Leu His Ser
            180                 185                 190

Arg His Thr Glu Leu Lys Glu Lys Leu Arg Ser Ile Asn Gln Gly Leu
    195                 200                 205

Asp Arg Leu Arg Arg Val Ser His Gln Gly Tyr Ser Thr Glu Ala Glu
    210                 215                 220

Phe Glu Glu Pro Arg Val Ile Asp Leu Trp Asp Leu Ala Gln Ser Ala
225                 230                 235                 240

Asn Leu Thr Asp Lys Glu Leu Glu Ala Phe Arg Glu Glu Leu Lys His
            245                 250                 255

Phe Glu Ala Lys Ile Glu Lys Phe Asn Phe Tyr Gln Lys Gln Leu Glu
            260                 265                 270

Ile Ala Phe Glu Lys Leu Arg His Ala Glu Ser Val Gly Asp Gly Glu
            275                 280                 285

Arg Val Ser Arg Ser Arg Glu Lys Phe Ala Leu Leu Glu Gly Arg Thr
    290                 295                 300

Lys Glu Leu Gly Tyr Thr Val Lys Lys His Leu Gln Asp Leu Ser Gly
305                 310                 315                 320

Arg Ile Ser Arg Ala Arg His Asn Glu Leu
            325                 330
```

RAP VARIANTS FOR DRUG DELIVERY AND METHODS OF USE THEREOF

FEDERALLY SPONSORED RESEARCH

This invention was made with Government support under NIH grant number HL61001. Accordingly, the Government may have certain rights in this invention.

RELATED APPLICATIONS

This application is a National Stage application of PCT/US2008/013542, filed Dec. 10, 2008, which claims the benefit of priority under 35 U.S.C. §119 of U.S. provisional application Ser. No. 61/007,124, filed Dec. 10, 2007, and U.S. provisional application Ser. No. 61/008,827, filed Dec. 21, 2007, entitled "RAP VARIANTS FOR DRUG DELIVERY," each of which are incorporated herein by reference in their entirety.

FIELD OF THE INVENTION

The present invention relates to stabilized RAP variants, conjugates thereof, and methods of use of the stabilized RAP variants and conjugates.

BACKGROUND OF THE INVENTION

The 39 kD receptor-associated protein (RAP) is an ER-resident protein that was originally identified because it co-purified with the low-density lipoprotein related protein (LRP1) (Strickland et al., 1991 J. Biol. Chem. 266:13364-13369). Subsequent functional studies established that RAP plays a role in ensuring efficient delivery of LRP1 and other transmembrane proteins of the low-density lipoprotein receptor family of proteins (LDLRFP) to the cell surface (Lee et al., 2006 Moll Cell 22: 423-430). In addition, through binding to proteins of the LDLRFP, RAP can deliver therapeutic proteins and polypeptides into cells and across the blood brain barrier (Pan et al., 2004 J Cell Science 117: 5071-5078). Furthermore, RAP can attenuate the function of proteins of the LDLRFP, which can result in the suppression of cell activity and an increase of the in vivo half-life of LDLRFP ligands.

RAP consists of three domains of approximately 100 residues each. The affinity of the third domain of RAP (RAP-D3) for LRP1 is at least an order of magnitude greater than that of the other RAP domains. At neutral pH, wild-type (WT) RAP-D3 is highly helical, but it undergoes a cooperative thermal unfolding transition at 42° C., and a pH-induced unfolding transition at a pH of 6.3, and loses its ability to bind to members of the LDLRFP, including LRP1.

There remains a need for stabilized variants of RAP for improved transport of therapeutic compounds and therapeutic polypeptides into cells and across the blood brain barrier. In addition, there remains a need for stabilized variants of RAP to suppress cell activity and to increase the in vivo half-life of LDLRFP ligands.

SUMMARY OF THE INVENTION

Aspects of the invention relate to stabilized Receptor Associated Protein (RAP) variants and uses thereof. In some embodiments a stabilized RAP variant is a stabilized domain 3 RAP variant (a variant in domain 3 that stabilizes the protein).

An embodiment of the invention comprises a stabilized domain 3 Receptor Associated Protein (RAP) variant, wherein the stabilized domain 3 RAP variant has either a higher melting temperature than wild type (WT) RAP, an increased resistance towards low-pH induced denaturation when compared to WT RAP, an increased resistance towards protease degradation when compared to WT RAP, or an increased in vivo half-life when compared to WT RAP.

In some embodiments the composition comprises a stabilized domain 3 RAP variant that is either a full-length, or less than a full-length RAP. In some embodiments the composition comprises a stabilized domain 3 RAP variant that consists of domain 3.

In some embodiments domain 3 of the stabilized domain 3 RAP variant is modified when compared to WT RAP. In some embodiments at least one amino acid of domain 3 of the stabilized domain 3 RAP variant is mutated. In some embodiments at least one of the amino acids that interacts with a protein of the low density lipoprotein receptor family of proteins (LDLRFP), when RAP is bound to a protein of the LDLRFP, is either modified or mutated. In some embodiments the protein of the LDLRFP is LRP1. In some embodiments at least one of the amino acids at the interfaces of the helices is either modified or mutated. In some embodiments at least one of the histidine residues (e.g., 1, 2, 3, 4) in at least one of the RAP domains is replaced with a hydrophobic residue, a neutral residue or phenylalanine. In some embodiments, His 257 or His 259 or His 268 or His 290 is replaced by any amino acid (for example a hydrophobic residue or a neutral residue). In some embodiments, His 257 or His 259 or His 268 or His 290 is replaced by Phe. In some embodiments, His 257 and His 259, His 268 and His 290, or His 257, His 259, His 268 and His 290 are replaced by Phe.

In some embodiments the invention provides stabilized RAP variants with one or more mutations in other domains (e.g., a His to Phe mutation in domain 1, or Tyr to Ala mutation in domain 2).

In some embodiments, the invention provides stabilized RAP variants that are stabilized chemically, for example by chemical reinforcement of an alpha helix containing one or more non-natural amino acids. Such techniques can be referred to as "stapling." Examples of techniques for stabilizing proteins by "stapling" involving non-natural amino acids are described, for example, in Walensky et al., Mol. Cell., 2006, Oct. 20, 24(2): 199-210: A stapled BID BH3 helix directly binds and activatres BAX, the technical disclosures of which are incorporated herein by reference in their entirety. It should be appreciated that RAP variants containing non-natural amino acids can be produced synthetically.

In some embodiments a stabilized RAP variant is either conjugated to a therapeutic compound or fused to a therapeutic polypeptide to produce a fusion peptide.

In some embodiments a stabilized RAP variant may be engineered to contain one or more amino acids (e.g., cysteines) that can be modified (e.g., via a redox reaction) for conjugation to a compound (e.g., a therapeutic compound). In some embodiments a compound may be conjugated to a cysteine in the RAP protein via a linker that can be subsequently hydrolyzed (e.g., under acidic conditions inside a cell after the compound has been delivered along with the RAP variant).

Accordingly, some embodiments comprise a method for transporting a therapeutic compound into a target cell comprising contacting the target cell with a stabilized RAP variant described herein (e.g., conjugated or fused to the therapeutic compound).

Additional embodiments comprise a method for transporting a therapeutic polypeptide into a target cell comprising contacting the target cell with a stabilized RAP variant fusion peptide. In some embodiments, the target cell is either a cell of the CNS or a liver cell. In some embodiments, the target cell is in a subject and either the composition, or the fusion peptide, is administered to the subject.

Some embodiments comprise a method for attenuating the activity of a cell expressing one or more proteins of LDLRFP comprising either administering to a subject, or contacting a cell expressing one or more proteins of LDLRFP, with an effective amount of an above mentioned composition. In some embodiments the protein of the LDLRFP is LRP1.

Further embodiments comprise a method for treating a cancer in a subject comprising administering to a subject an effective amount of a composition of the invention to treat the cancer.

Additional embodiments comprise a method for increasing the half-life of a ligand of a protein of the LDLRFP in a subject comprising administering to a subject an effective amount of a composition of the invention to increase the half-life of the ligand of the protein of the LDLRFP. In some embodiments the protein of the LDLRFP is LRP1.

Further embodiments comprise a method for treating a bone disorder in a subject comprising administering to a subject an effective amount of a composition of the invention to treat the bone disorder.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

DETAILED DESCRIPTION

Figure 1:
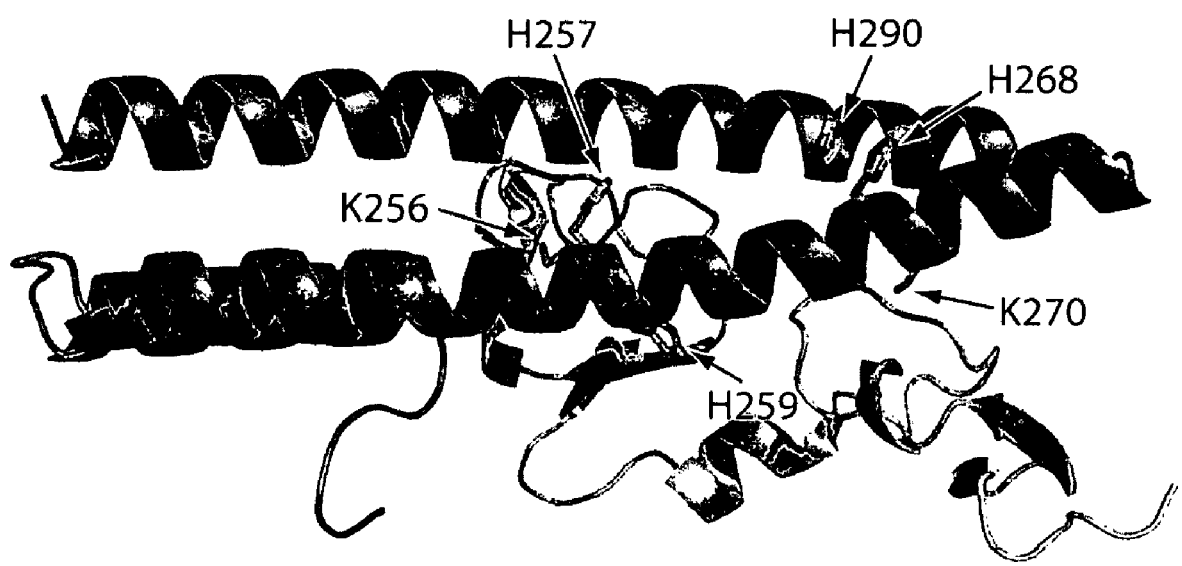
FIG. 1 shows the overall structure of LA3-4/RAP-D3 complex (PDB ID code 2FCW) indicating histidine residues of RAP-D3 buried in the inter-helical interface. The LA3-4 (light grey) and RAP-D3 (dark gray) polypeptide chains are illustrated as ribbons. Key interfacial residues, histidines and lysines, are highlighted as sticks.

In one aspect the invention provides stabilized variants of Receptor Associated Proteins (RAP). In some embodiments the stabilized RAP variants have increased resistance to thermal and/or low pH-induced unfolding. In some embodiments the stabilized RAP variants have increased resistance to proteases. In some embodiments the stabilized RAP variants have an increased in vivo half life. In some embodiments the RAP variant comprises a stabilized domain 3 RAP variant. However, stabilized RAP variants may include one or more stabilizing mutations, in one, two or all three domains. The stabilizing mutations may be in the helical bundle of a domain. In some embodiments a stabilizing mutation may result in one or more His residues being replaced with a non-polar hydrophobic residue, for instance Phe, Trp, Tyr, Val, etc., that stabilize the protein. It should be appreciated that any combination of hydrophobic residues replacing different His residues may be used.

Stabilized RAP variants may be attached, fused or conjugated to one of more moieties of interest, including therapeutic and diagnostic moieties.

RAP binds a variety of proteins of the low-density lipoprotein receptor family of proteins (LDLRFP) and can be transported into LDLRFP expressing cells through transcytosis. Proteins of LDLRFP include LDL receptor-related protein 1 (LRP-1), VLDLR, LDLR and others. In addition, it has been shown that RAP-conjugates can be delivered into cells. Accordingly, in one aspect the invention provides methods for the delivery of therapeutic compounds or therapeutic peptides into cells expressing proteins of the low-density lipoprotein receptors (LDLRFP). In some embodiments the invention provides methods for the delivery of therapeutic compounds or therapeutic polypeptides across the blood-brain barrier (BBB). In some embodiments the invention provides methods for the delivery of therapeutic compounds or therapeutic polypeptides to the liver. Aspects of the invention may be used to deliver one or more diagnostic agents into cells expressing proteins of the LDLRFP and/or liver cells and/or across the BBB.

RAP can also act as an attenuator of the function of proteins of the LDLRFP. In one aspect the invention provides methods for the suppression of cell activity through the administration of stabilized RAP variants. In some embodiments the stabilized RAP variants of the invention can be used to treat cancer. In some embodiments the stabilized RAP variants of the invention can be used to treat a bone disorder.

Through binding to a protein of the LDLRFP, RAP can act as an inhibitor of the clearance of natural ligands of proteins of the LDLRFP. In one aspect the invention provides methods to increase the in in vivo half-life of ligands of proteins of the LDLRFP through the administration of the stabilized RAP variants of the invention.

It should be appreciated that aspects of the invention that are described herein in the context of specific proteins of the LDLRFP are equally applicable to other members of the LDLRFP, unless specifically stated.

RAP is an antagonist and molecular chaperone of proteins of LDLRFP. During the delivery of proteins of the LDLRFP to the cell surface RAP acts as a chaperone that binds tightly at near-neutral pH early in the secretory pathway, but then dissociates from bound receptors at the lower pH of the Golgi compartment. The modulation of affinity by pH is believed to play an important role in the function of RAP as an escort protein for proteins of the LDLRFP by preventing premature intracellular binding of ligands to the receptors during the routing stage of receptor transport, thus enabling delivery of mature receptors to the cell surface.

Figure 3:
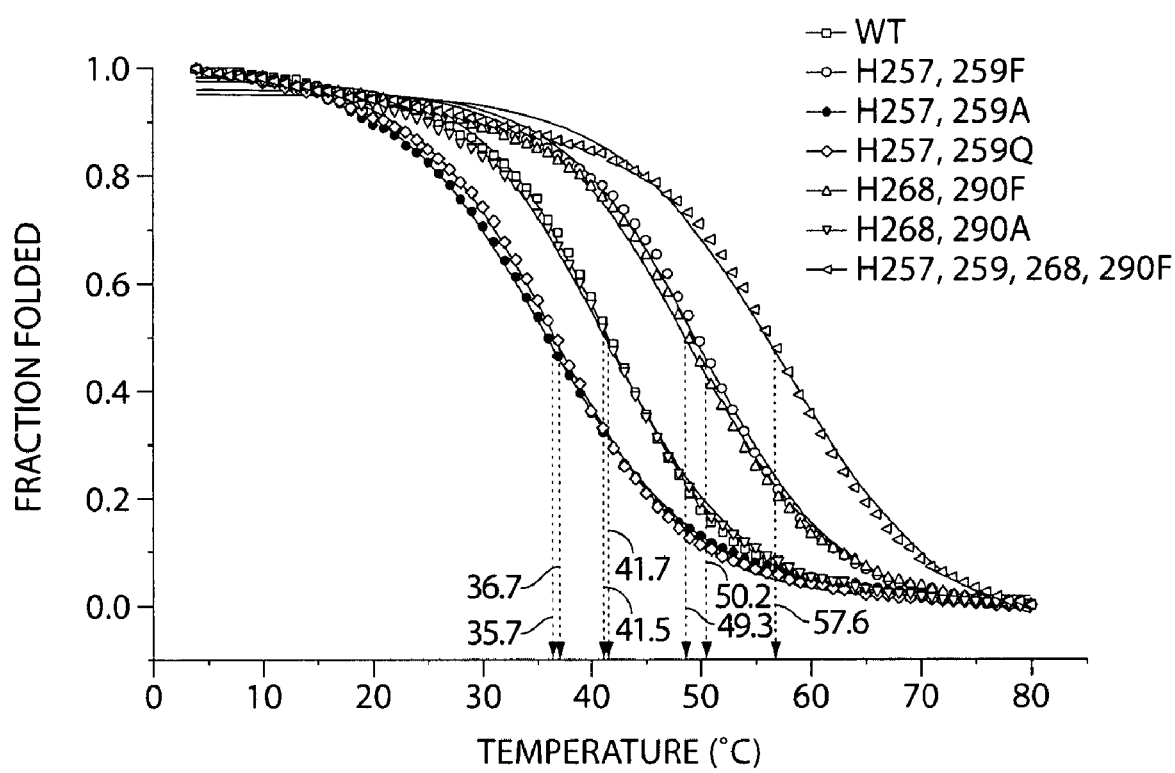
FIG. 3 illustrates temperature-induced unfolding of RAP-D3 WT and mutants monitored by changes in molar ellipticity at 222 nm. The apparent $T_m$ of RAP-D3 H257,259A or Q mutants is less than that of wild-type (~36° C.), while that of the H268,290A mutant is similar to wild-type (~42° C.). The apparent $T_m$ of both H-to-F double mutants is greater than that of wild-type (~50° C.), whereas that of the H-to-F quadruple mutant is much greater than wild-type (~58° C.).
Figure 4:
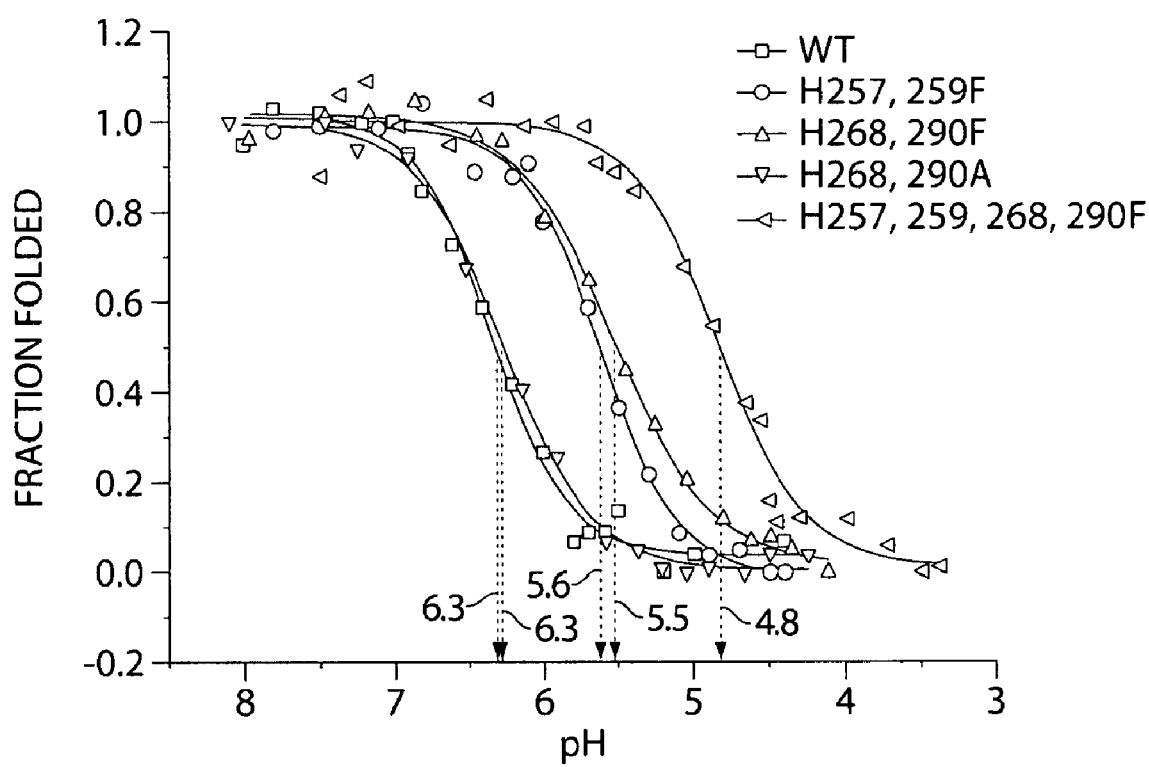
FIG. 4 shows the pH-induced unfolding of RAP-D3 WT and mutants monitored by changes in molar ellipticity at 222 nm, 30° C. The pH at which half of the helical content is lost for both the wild-type and H268,290A mutant is 6.3, whereas for the H-to-F double mutants and quadruple mutants it is 5.5 and 4.8, respectively.
Figure 5:
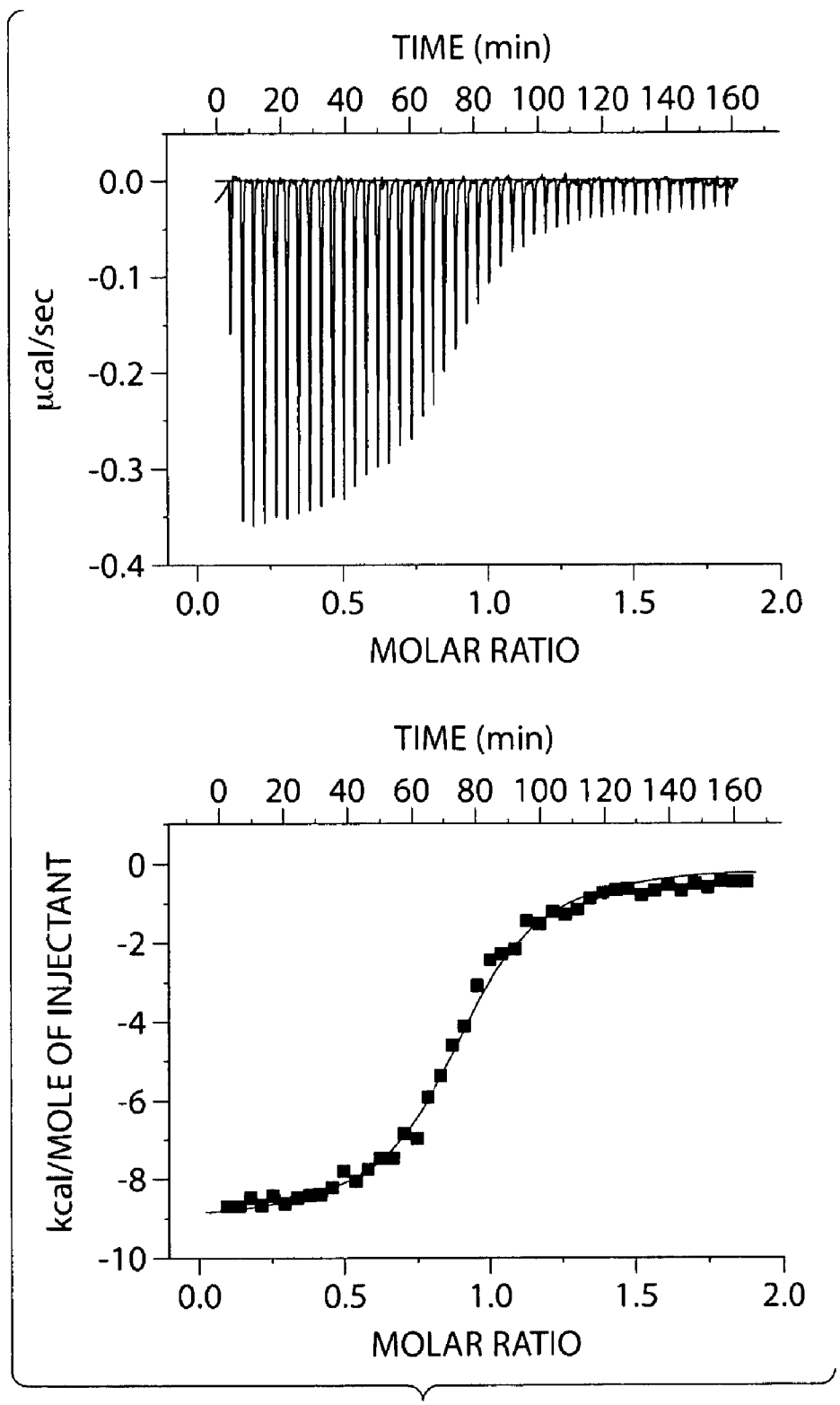
FIG. 5 depicts Isothermal Titration Calorimetry measurement for binding of RAP-D3 WT to LA3-4. Curve fitting to a single site-binding model (bottom panel) yields a value for $K_D$ of 480 nM. Each peak (top panel) and point (bottom panel) indicates a 6 µl aliquot of 180 µM RAP-D3 WT titrated into 20 µM LA3-4 in 20 mM HEPES, pH 7.35, containing 50 mM NaCl and 5 mM $CaCl_2$. Measurements were acquired at 25° C.
Figure 6A:
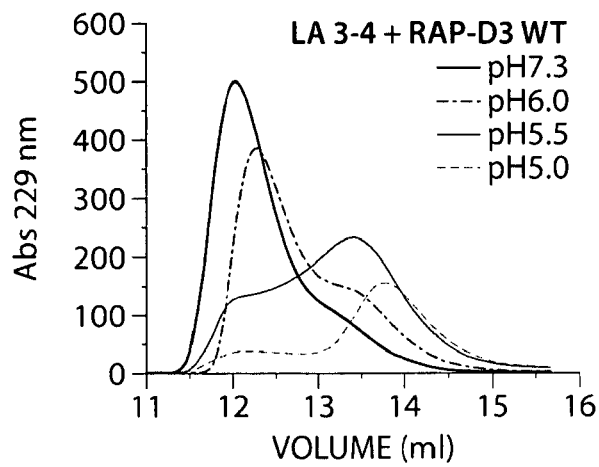
FIGS. 6A-6C illustrate pH-dependent dissociation of RAP-D3 protein variants from LA3-4. Analytical size-exclusion chromatograms for (A) RAP-D3 WT, (B) RAP-D3 H257,259F, and (C) RAP-D3 H257,259,268,290F (Quad H:F) in complex with LA3-4. Dissociation of wild-type RAP-D3 from LA3-4 is evident at pH 6.0, while that of the H257, 259F mutant is evident at pH 5.0. Dissociation of RAP-D3 Quad H:F is not apparent, even at pH 5.0.
Figure 6B:
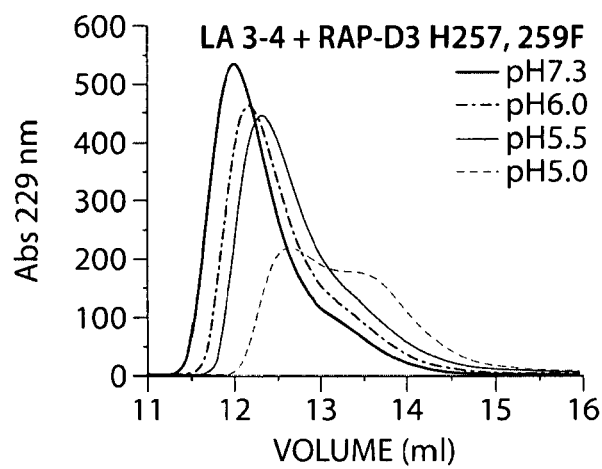
Figure 6C:
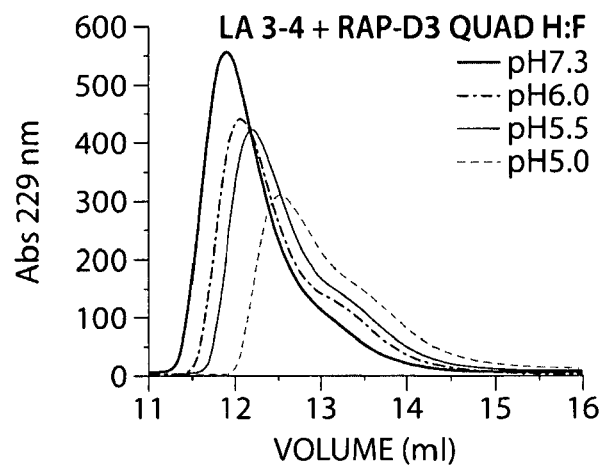
Figure 7A:
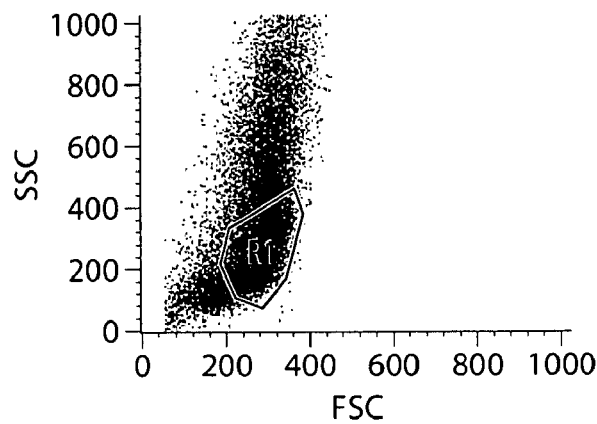
FIGS. 7A-7C show the response of endogenous LRP-1 to treatment with RAP quadruple H:F mutant. (A) Flow cytometry forward (X-axis) and side scatter (Y-axis) dot plot illustrating cell population selected for subsequent analysis (R1). (B) Gating for GFP-positive cells (R2). (C) Flow cytometry plot illustrating endogenous LRP-1 cell surface expression after gating on live, GFP-positive cells. HepG2 cells transfected with plasmids expressing GFP and wild-type, full-length RAP have similar expression levels of LRP-1 as those transfected with plasmids expressing GFP and empty vector, while cells transfected with plasmids expressing GFP and full-length RAP harboring H257,259,268,290F mutations (Quad H:F) have reduced expression levels.
Figure 7B:
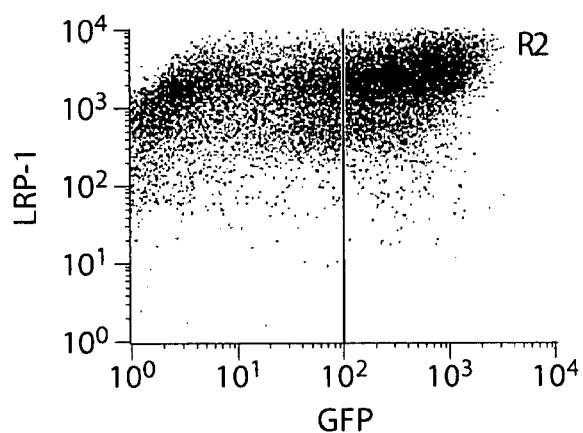
Figure 7C:
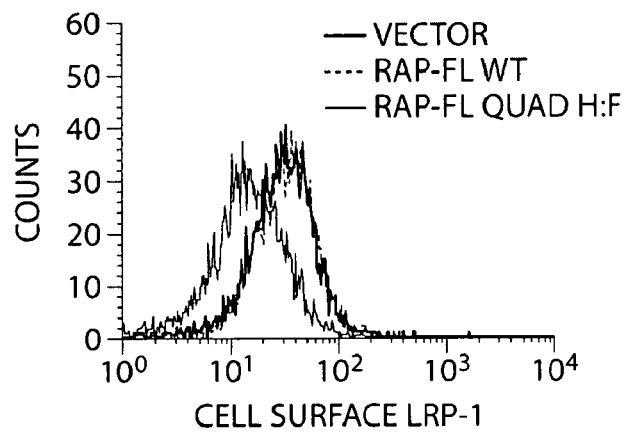
Figure 8A:
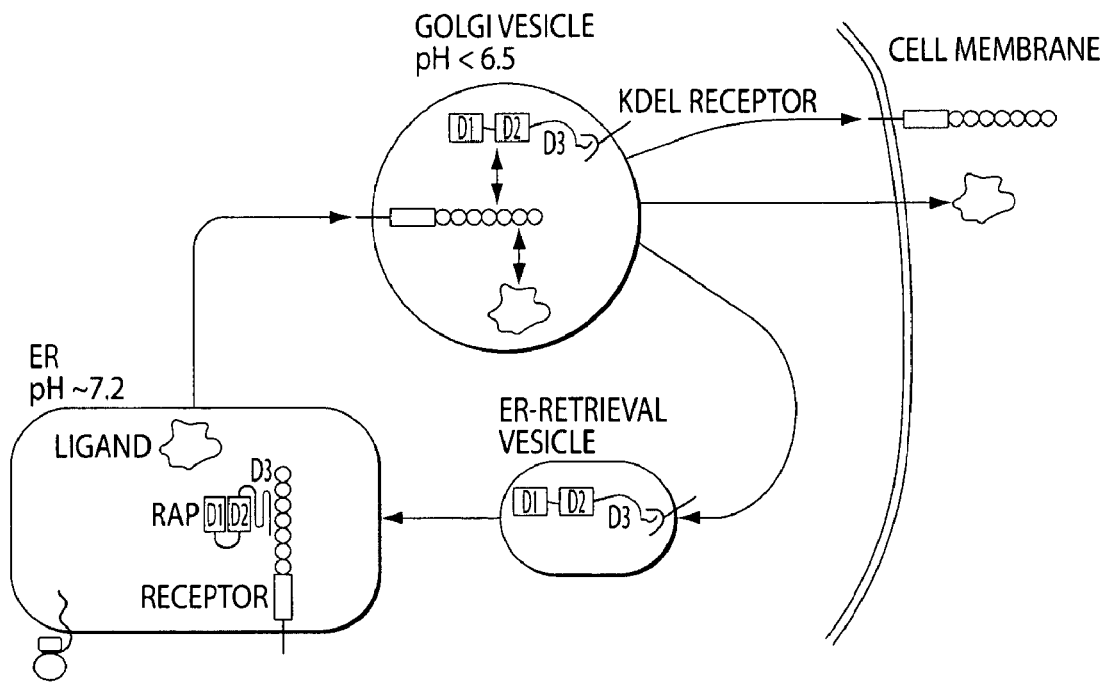
FIGS. 8A-8B illustrate a non-limiting embodiment for a model for the effect of RAP on maturation of proteins of the LDLRFP. (A) Wild-type RAP forms a complex with the ligand binding domain of the receptor in the neutral pH environment of the ER, thus preventing premature ligand association. The complex is transported to the Golgi and unfolding of RAP-D3 results in complex dissociation and exposes the C-terminal HNEL sequence of RAP in response to the low pH environment of the Golgi. RAP is recycled to the ER via recognition of its C-terminal HNEL sequence by the KDEL receptor, while receptor and ligands are exported to the cell surface. (B) RAP-D3 harboring histidine to phenylalanine mutations does not unfold, and therefore does not dissociate from the receptor in the Golgi. This may result in either aggregation or degradation of the complex and proteins of the LDLRFP may still be exported to the cell surface.
Figure 8B:
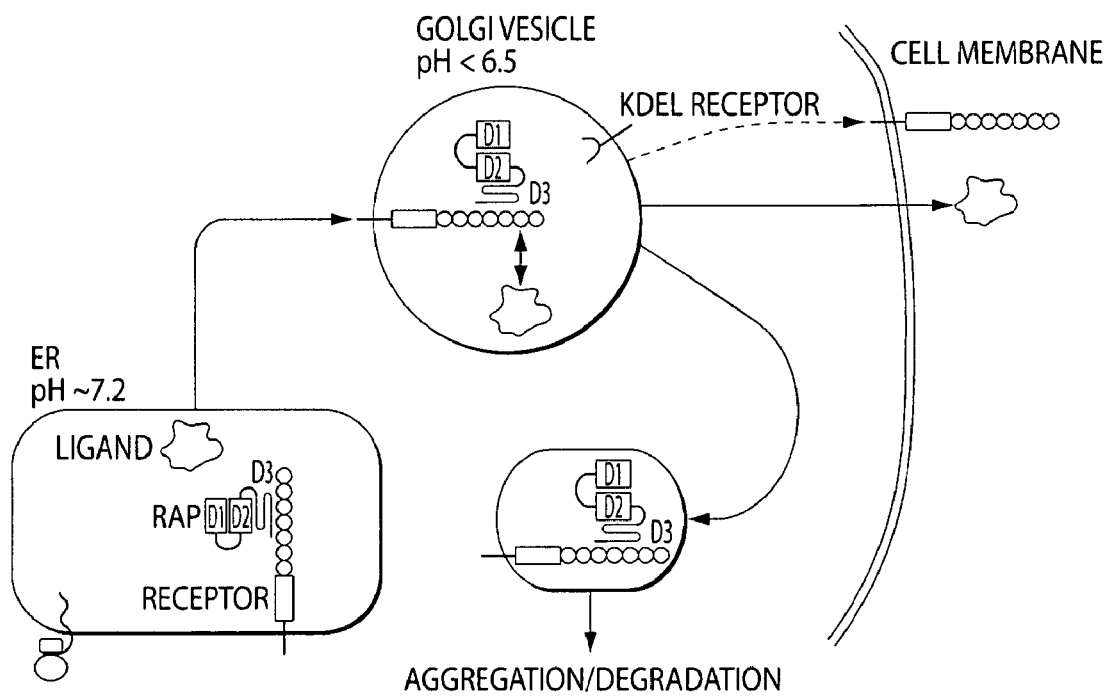
Figure 9A:
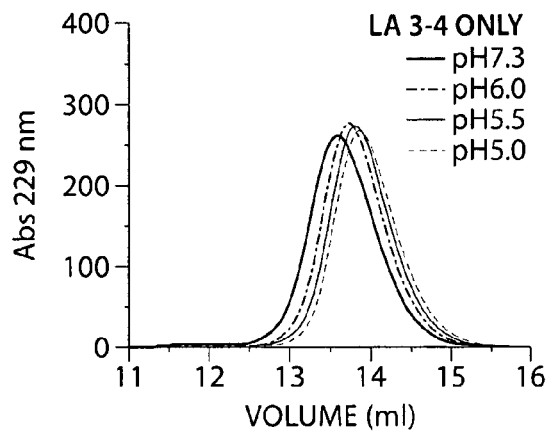
FIGS. 9A-9D show the dissociation behavior of the LRP-1-RAP complexes at various pH.
Figure 9B:
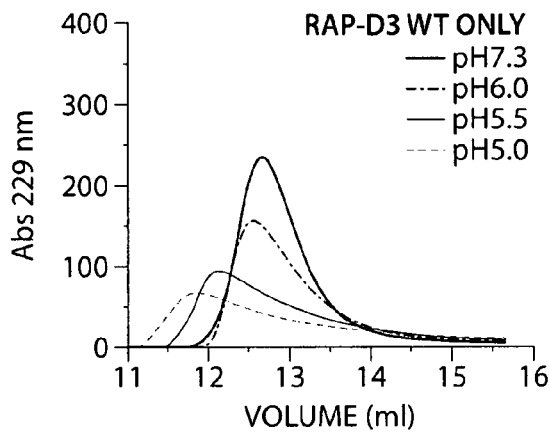
Figure 9C:
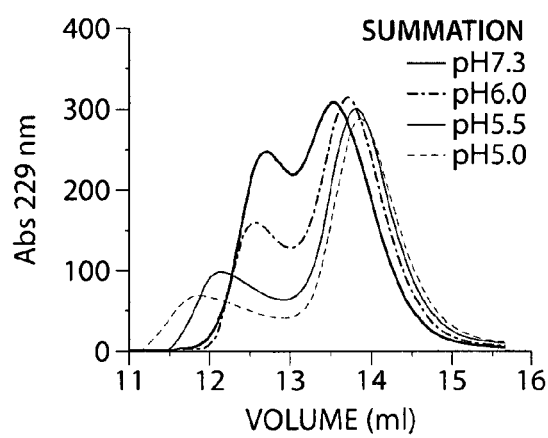
Figure 9D:
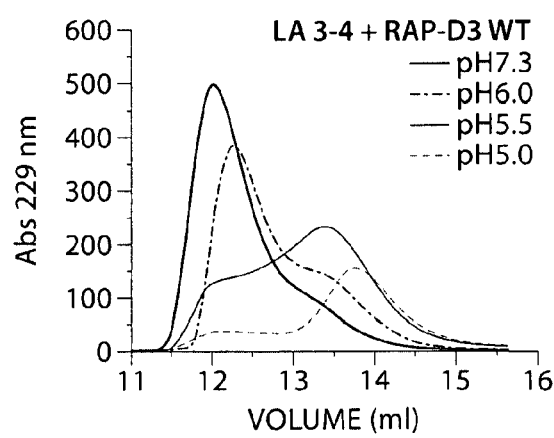

RAP is a three-domain protein, with each of the domains independently adopting a three-helix bundle structure (Lee et al., Protein Sci. 16, 1628-40). The third domain of RAP (RAP-D3) exhibits the highest affinity for proteins of the LDLRFP family, and is sufficient to reconstitute the chaperone activity of the full-length protein. To be able to function as a chaperone WT RAP is not particularly stable to extremes of temperature or pH, melting at 42° C., and unfolding at a pH of approximately 6.3 (FIGS. 3, 4). In some embodiments stabilized RAP variants of the invention have a melting temperature at or above 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100° C., or higher. In some embodiments the stabilized RAP variants have an unfolding at or below pH 6.2, 6.1, 6.0, 5.9, 5.8, 5.7, 56, 5.5, 5.4, 5.3, 5.2, 5.1, 5.0, 49., 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, or lower.

Exogenously applied RAP can be endocytosed efficiently by proteins of the LDLRFP. However, because of its low melting temperature and pH sensitivity, WT RAP is not particularly suited as an in vivo delivery particle. The invention provides stabilized RAP variants and stabilized domain 3 RAP variants, and uses thereof for in vivo delivery.

In some embodiments the stabilized RAP variants have one stabilized domain. In some embodiments domain 3 of RAP is stabilized. In some embodiments the stabilized RAP variants have two stabilized domains. In some embodiments all three domains of RAP are stabilized. In some embodiments the loops between the domains are stabilized. In some embodiments the N-terminal and C-terminal sequences are outside of the domains are stabilized. In some embodiments at least one of the amino acids that interacts with a protein of the low density lipoprotein receptor family of proteins (LDLRFP), when RAP is bound to the protein of LDLRFP, is either modified or mutated. It should be appreciated that any combination of stabilization is also embraced by the invention. For instance, an example of a stabilized RAP variant of the invention is a RAP variant that has a stabilized domain 1 and a stabilized loop between domain 2 and domain 3.

In some embodiments the RAP variants are stabilized through the introduction of mutations. For instance, amino acids that are susceptible to protease degradation can be replaced by amino acids resistant to protease degradation. It should be understood that in making these changes the function of the RAP variant is preferably not compromised. Other mutations embraced by the invention are mutations that result in the increase of the stability of secondary structure. For instance, replacing a valine residue by alanine in an alpha-helical structure will result in a stabilization of the secondary structure. Secondary structure can also be stabilized by the introduction of amino acids that improve the charge distribution of the secondary structure including the introduction of salt bridges. RAP variants can also be stabilized by minimizing the length of the loops between the domains.

In some embodiments the RAP variants are stabilized through the introduction of modifications. For instance, charges between amino acid side chains that repel each other can be chemically or biologically (e.g., enzymatically) modified to remove one of the repelling charges. For instance, an amino acid with a negatively charged side chain can be modified to remove the charge on the side chain. Additional modifications that can be introduced include cross links, helix clamps, etc., or any combination thereof.

In some embodiments proteins of the LDLRFP bind to RAP via one or more LDL receptor type-A (LA) repeats on the LDLRFP. Binding to RAP typically involves two or more LA repeats. In the LDLR-RAP domain 3 (RAP-D3) binding complex, the RAP domain forms a three-helix bundle and contacts the receptor fragment at two docking sites. This binding pattern seems to be universal for binding of RAP-D3 to all proteins of the LDLRFP (Fisher et al., Molecular Cell 22; 277-283). The interface at each docking site is dominated by electrostatic interactions between conserved acidic residues on the binding domain of proteins of the LDLRFP and a lysine from helix 2 of the RAP-D3 helix bundle.

In some embodiments the three helix bundle of the binding domain is stabilized. In some embodiments the interaction between the bundles of the three helices is stabilized. In some embodiments residues involved in the interaction between the helices are modified or mutated. In some embodiments the residues between helix 2 and 3 are modified. In some embodiments one or more histidine residues in the interface between helix 2 and 3 are replaced. In some embodiments one or more histidine residues are replaced with hydrophobic residues. In some embodiments the hydrophobic residues are Phe, Val, Leu, Ile or Trp. In some embodiments one or more histidine residues are replaced with neutral residues. In some embodiments one or more histidine residues are replaced with phenylalanine. In some embodiments one or more of residues His 257, His 259, His 268 and His 290 are replaced (e.g., with A, W, V, Y, etc.). In some embodiments His 257 and His 259 are replaced. In some embodiments His 268 and His 290 are replaced. In some embodiments His 257, His 259, His 268 and His 290 are replaced. In some embodiments the His residues are replaced with alanine, phenylalanine, leucine, tryptophan, etc., or any combination thereof.

In some embodiments one or more of the histidines in domain 1 and/or domain 2 may be replaced (e.g., with A, F, L, W, V, Y, etc., and combinations thereof), in addition to, or instead of domain 3 mutations.

Any stabilized RAP variant is embraced by the invention, including proteins in which the loop has been removed, domains have been shuffled, etc., provided they comprise a stabilized domain and have the capacity to interact with proteins of the LDLRFP. In some embodiments the stabilized domain is a D3 domain. Minimized D3 domains that still maintain the capacity to bind to proteins of the LDLRFP are also embraced by the invention. For instance, Isbell et al., (2007, Biochem. Biophys. Res. Comm. 361: 758-762) have shown that D3 domains with truncated N- and C-termini still maintain the capacity to bind to proteins of the LDLRFP. Residues 206-242 and 313-323 were removed without sacrificing capacity to bind to proteins of the LDLRFP.

It should be appreciated that one or more of the stabilizing mutations described herein (e.g., one or more His mutations) may be combined with one or more additional mutations or chemical modifications known in the art (e.g., W2007/035716, WO2006/138343 and US 2006/0029609, all of which are incorporated by reference). Also, it should be appreciated that the mutations described here in the context of the human RAP protein may be made in equivalent RAP proteins from other species (e.g., one or more His mutations in RAP proteins from another species). Other species include horse, rat, pig, sheep, dog, etc.

Functional Applications: Transcytosis

RAP binds a variety of proteins of the low density lipoprotein receptor family of proteins (LDLRFP), including LDLR, VLDLR, LRP1, LRP1B, megalin, apoER2, LRP4 and sortilin. Other members of the proteins of the LDLRFP are MEGF7, LRP5, LRP6 and LR11. RAP also binds lipoprotein lipase, involved in the cellular uptake of lipoprotein constituents. Exogenously applied RAP can be endocytosed efficiently by all proteins of the LDLRFP. RAP has been shown to be functional in both N- and C-terminal fusions with other proteins (Pan et al., 2004 J. Cell Science 117: 5071-5078). RAP has a higher permeability than melanotransferrin or transferrin, which shows that proteins of the LDLRFP can function as a high capacity transport system (Pan et al., 2004J. Cell Science 117: 5071-5078). Thus, RAP is a useful vehicle to bring proteins, including therapeutic polypeptides into cells. In some embodiments the invention provides for conjugates of stabilized RAP variants to therapeutic compounds. Therapeutic compounds can be of any nature and include small molecules, nucleic acids and polypeptides. In some embodiments the conjugates of the invention are stabilized RAP-polypeptide fusion proteins. In some embodiments the invention provides methods for introducing therapeutic and/or diagnostic compounds into cells, that express one or more proteins of the LDLRFP. In some embodiments the invention provides methods for introducing therapeutic polypeptides into such cells.

Assays to evaluate the capacity of a stabilized RAP variant to introduce a therapeutic compounds are available, according to aspects of the invention. For instance, screening for stabilized RAP variants that can function as a transporter can be done through an endocytosis dependent toxicity assay or by assaying the distribution of a labeled compound (e.g., radioactive or fluorescent) as a substitute therapeutic compound.

It should be appreciated that expression patterns of the proteins of the LDLRFP can differ between cell types and target organs. Thus, a therapeutic compound or therapeutic polypeptide can be targeted to a specific cell or a specific organ based on the expression level of one or more proteins of the LDLRFP in the target cell or the target organ. For instance, certain cancer cells have expression patterns of one or more proteins of the LDLRFP that differ from healthy cells. Thus, a therapeutic window is available for the administration of therapeutic compounds to cancer cells.

In addition, it should be appreciated that there are differences in expression levels between the various proteins of the LDLRFP, when multiple cell types and organs are compared. For instance, while the VLDL receptor protein of the LDLRFP may be highly expressed in brain cells another receptor protein of the LDLRFP may have a much lower expression level in the same cell type.

It should also be appreciated that while WT RAP is likely to be capable of binding to all proteins of the LDLRFP, there are variations in binding affinity of RAP to the various proteins of the LDLRFP. For instance, WT RAP may have higher affinity for LRP-1 than for MEGF7. RAP mutants have been engineered that have a higher affinity for one or more specific proteins of the LDLRFP, and these mutants can be used to specifically target one or more proteins of the LDLRFP, even when other proteins of the LDLRFP family are present, or to target cells expressing the one or more specific proteins of the LDLRFP (e.g., WO 2007/035716 Zankel et al.). The invention embraces stabilized variants of these RAP mutants that can specifically target one or more proteins of the LDLRFP.

Brain

Among the proteins of the LDLRFP, LDL receptor-related protein 1 (LRP1) and LDL receptor-related protein 2 (LRP2 or megalin) have been shown to possess the ability to mediate transcytosis of ligands across the brain capillary endothelium. Since RAP serves as a vehicle of receptor-mediated transcytotic delivery RAP can be used to transport therapeutic compounds and therapeutic peptides into the brain in vivo. Thus, stabilized RAP variants of the invention can be used to treat a variety of neurological disorders and disorders of the Central Nervous System. Therapeutic compounds and therapeutic polypeptides can be conjugated to RAP to provide efficient transport into the brain.

The stabilized RAP variants of the invention are well suited as vehicles for transport across the blood-brain barrier. The resistance of the stabilized RAP variants to extremes of temperature and pH makes them ideal candidates for use as targeted delivery agents. The ability of RAP to cross the blood-brain barrier makes RAP, including stabilized RAP variants and stabilized domain 3 RAP variants particularly valuable as agents for delivery of therapeutic compounds and therapeutic polypeptides to the brain and other privileged sites in the CNS. In addition, this ability also makes stabilized RAP and RAP-D3 valuable as agents for potentiating the activity of antithrombotic agents that are used to treat stroke and are normally cleared by LDLRFP members in the brain. Non-limiting examples of antithrombotic agents that may be potentiated by variants of the invention include urokinase plasminogen activator (uPA), tissue plasminogen activator (tPA), or combinations thereof.

RAP has been shown to rescue neurodegeneration when infused into the lateral ventricle of the brain along with apoE3 (Veinbergs et al., 2001 Exp. Neurol. 170: 15-26). In some embodiments the stabilized RAP variants of the invention are used to rescue neurodegeneration. The stabilized RAP variants of the invention may be administered to patients suffering from one or more symptoms of a neurodegenerative disorder. In one embodiment, stabilized RAP and RAP-D3 variants may antagonize the neurodegeneration-promoting effects of the ApoE4 polymorphism. Accordingly, RAP variants of the invention may be administered to subjects having or at risk of a disease (e.g., Alzheimer's Disease) associated with ApoE4 in order to slow or prevent the development of the disease. In some embodiments, and without wishing to be bound by theory, RAP variants of the invention may bind to receptors that bind to ApoE and thereby compete with and reduce ApoE4 uptake by neuronal cells and oligodendrocytes.

Liver

It has been shown that rats injected with RAP peptides accumulate these peptides in the liver (Isbell et al., 2007 Biochem. Biophys. Res. Comm. 364: 614-619). In some embodiments stabilized RAP variants of the invention are used to introduce therapeutic compounds and therapeutic polypeptides into the liver. Non-limiting examples of liver therapeutic compounds and therapeutic polypeptides include anti-inflammatories, anti-virals and antibodies, as well as anti-cancer agents (for treating hepatocellular carcinoma, for example).

Functional Applications: Inhibition of Proteins of the LDL-RFP

RAP binds a variety of proteins of the LDLRFP, including LDLR, VLDLR, LRP1, LRP1B, megalin, apoER2, LRP4 and sortilin. RAP also binds lipoprotein lipase, involved in the cellular uptake of lipoprotein constituents. In some embodiments stabilized RAP variants can be used to inhibit, suppress or attenuate the activation of proteins of the LDLRFP. A variety of proteins bind to the same receptor domains of proteins of the LDLRFP as RAP. These proteins include alpha-2-macroglobulin, urokinase plasminogen activator complexed with plasminogen activator inhibitor-1 (uPA-PAI-1), reelin, human rhinovirus 1A and 2, vitellogenin and apoE. RAP has been shown to inhibit binding of these ligands to their receptors completely, thereby increasing the in vivo half-life of these proteins (ligands) (Isbell et al., 2007, Biochem. Biophys. Res. Comm. 364: 614-619). For instance, when administered intravenously, RAP prolongs the half-life of tissue-type plasminogen activator (tPA) which uses LRP1 as a clearance receptor (Warshawsky et al., 1993, J. Clin. Invest. 92: 937-944). Binding of RAP to proteins of the LDL-RFP can inhibit the clearance of other ligands of proteins of the LDLRFP from the blood. The stabilized RAP variants of the invention are particularly well suited for this task. Because of their higher stability the RAP variants of the invention will be more resistant to proteases and have a longer half-life in vivo. The RAP variants of the invention thus have increased ability to act as an antagonist/inhibitor and prevent other ligands of proteins of the LDLRFP from being processed, thereby increasing their half-life. Thus, in some embodiments the stabilized RAP variants of the invention are used to increase the half-life of ligands of proteins of the LDLRFP.

In some embodiments the stabilized RAP variants of the invention are protective against neuronal injury. Vasogenic edema induced by tissue plasminogen activator (tPA) in cases of neuronal injury or certain types of embolic stroke depends on interactions between tPA and LRP-1. This interaction can be blocked by anti-LDLR antibodies or by soluble RAP, which is likely to be competing for tPA binding in this context (Yepes, 2003 J. Clin. Invest. 112: 1483-1485). In one embodiment of the invention, the stabilized RAP variants are used to treat neuronal injury.

Cancer

Proteins of the LDLRFP have been found to be overexpressed in invasive breast cancer cell lines. The migratory and invasive abilities of a cancer cell line has been shown to be inhibited by the administration of RAP (Li et al., 1998 Invasion and Metastasis 18: 240-251). In some embodiments stabilized RAP variants of the invention are be used to suppress, attenuate or inhibit the activity (e.g., inhibit the growth or proliferation) of cell lines that express or overexpress proteins of the LDLRFP, including cancer cells.

Osteoporosis

In some embodiments the stabilized RAP variants can be used to treat bone disorders. One of the proteins of the LDL-RFP RAP can bind to is the LPR5 receptor, which plays a role in Wnt signaling, thereby regulating osteoblast differentiation, osteoclast activity and bone deposition. It has been shown that agents that bind to LRP5 may counter the effect of osteoporosis (Westendorf et al., 2004 Gene 341: 19-39). In some embodiments of the invention stabilized RAP variants are used to suppress osteoporosis.

Combination Therapy

Stabilized variants of the invention (e.g., stabilized RAP and/or RAP-D3) may be combined with one or more other therapeutic agents as described herein. For example, combinations with uPA, tPA, or both may be used to treat symptoms of stroke.

It should be appreciated that in any of the embodiments described herein, stabilized RAP variants having at least one additional substitution, deletion or insertion are also useful according to the invention. As used herein, a "conservative amino acid substitution" or "conservative substitution" refers to an amino acid substitution in which the substituted amino acid residue is of similar charge as the replaced residue and is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). The term "conservative amino acid substitution" also refers to the use of amino acid analogs or variants.

Methods for making amino acid substitutions, additions or deletions are well known in the art. The terms "conservative substitution", "non-conservative substitutions", "non-polar amino acids", "polar amino acids", and "acidic amino acids" are all used consistently with the prior art terminology. Each of these terms is well-known in the art and has been extensively described in numerous publications, including standard biochemistry text books, such as "Biochemistry" by Geoffrey Zubay, Addison-Wesley Publishing Co., 1986 edition, which describes conservative and non-conservative substitutions and properties of amino acids which lead to their definition as polar, non-polar or acidic.

In some embodiments the stabilized RAP variants and conjugated stabilized RAP variants can be used to treat one or more diseases or conditions of the CNS (e.g., the brain and/or spinal cord). In some embodiments the stabilized RAP variant is conjugated to a therapeutic compound that can be used to treat a disease or condition of the CNS. non-limiting examples of therapeutic compounds that can treat a disease of the CNS include antiviral, antibacterial, antifungal, anti-cancer and compounds with a neuronal function. In some embodiments the stabilized RAP variant is conjugated to a therapeutic polypeptide that can be used to treat a disease or condition of the CNS. Non-limiting examples of therapeutic polypeptides that can treat a disease of the CNS include antibodies, hormones, enzymes and other polypeptides with a neuronal function. The CNS includes the brain and spinal cord, which are delineated by the blood-brain barrier. The blood-brain barrier separates the CNS from the remainder of the body and circulation and controls passage of substances between the blood and the CNS. Methods of the invention are useful for treatment of brain and/or spinal cord diseases or conditions.

As used herein, the term "disease or condition of the CNS" means a disease or condition that is characterized by an abnormal brain region. Abnormal brain regions may include, for example, regions of brain tissue characterized by abnormal cell proliferation (e.g., malignant brain tumors), as well as regions of brain tissue physiologically affected by physical or biochemical injury, such as degenerative brain disease (e.g., Alzheimer's disease, Parkinson's disease), stroke, brain ischemia, infection, aging, or trauma. In some embodiments an abnormal brain region may be characterized by abnormal cell proliferation, and in particular, particular a neoplastic disease or malignancy, such as a cancer or a tumor. In some embodiments, an abnormal brain region is a malignant brain tumor. Among malignant brain tumors for which the inventive methods may be used are gliomas, which include any malignant glial tumor, i.e., a tumor derived from a transformed glial cell. About half of all primary brain tumors are gliomas. A glial cell is a cell that has one or more glial-specific features, associated with a glial cell type, including a morphological, physiological and/or immunological feature specific to a glial cell (e.g. astrocyte or oligodendrocyte), for example, expression of the astroglial marker fibrillary acidic protein (GFAP) or the oligodendroglial marker O4. Non-limiting examples of neoplastic diseases or malignancies treatable with a composition of the invention include gliomas, glioblastomas, glioblastoma multiforme (GBM; i.e., astrocytoma grade IV), oligodendroglioma, primitive neuroectodermal tumor, low, mid and high grade astrocytoma (i.e., astrocytoma grade II, anaplastic astrocytoma grade III, astrocytoma with oligodendrogliomal component), ependymoma (e.g., myxopapillary ependymoma papillary ependymoma, subependymoma, anaplastic ependymoma), oligodendroglioma, medulloblastoma, meningioma (i.e., atypical meningioma, malignant meningioma), pituitary tumors (i.e., pituitary adenoma), neuroblastoma, and craniopharyngioma. Other brain tumors that can be treated according to the present invention include, for example, acoustic neuroma (e.g., Neurilemmoma, Schwannoma, Neurinoma), chordoma, chordoma, CNS lymphoma, cysts, dermoid cysts, gangliocytoma, ganglioglioma, and hemangioblastoma.

In some embodiments of the invention, an abnormal brain tissue is a secondary or metastatic brain tumor (i.e., tumors that have spread to the brain from another part of the body). Non-limiting examples of metastatic brain tumors treatable with the composition of the present invention include cancers originating in breast, lung, kidney, colon, prostate, and skin (malignant melanoma).

In some embodiments of the invention, the disease or condition characterized by a region of abnormal brain tissue is a migraine, convulsions, an infection, mental illness (e.g., schizophrenia, depression), hypoxia, cerebral ischemia, cerebral palsy, degenerative brain disease, cerebrovascular disease, dyspnea, or encephalopathy. In yet other embodiments of the invention, a disease characterized by abnormal brain tissue is due to physical or biochemical injury, such as trauma.

In some embodiments of the invention, a disease or condition characterized by abnormal brain tissue is a migraine or headache. Migraines include, for example, migraine with aura, migraine without aura, masilar artery migraine, carotidynia, headache-free migraine, opthalmoplegic migraine, and status migraine.

In some embodiments of the invention, a disease or condition characterized by abnormal brain tissue is a convulsive disease or disorder. The term convulsion (i.e., seizure) refers to a sudden change in behavior due to an excessive electrical activity in the brain. Causes include, for example, epilepsy, head injury, infection or stroke. Types of epilepsy include, for example, general epilepsy, generalized cryptogenic or symptomatic epilepsies, generalized symptomatic epilepsies of nonspecific etiology, focal or partial epilepsy, temporal lobe epilepsies and frontal lobe epilepsies.

In some embodiments of the invention, a disease or condition characterized by abnormal brain tissue is a cerebrovascular disease. Cerebrovascular disease includes diseases in which neurological symptoms and signs result from disorders or diseases of the blood vessels (e.g., congenital anomalies and atherosclerosis). These include, for example, ischemic syndromes and hemorrhagic syndromes. Ischemic syndromes are disorders caused by insufficient cerebral circulation, and including for example, transient ischemic attacks (TIAs) and ischemic stroke. Hemorrhagic syndromes involve by bleeding into brain tissue, including the epidural, subdural, or subarachnoid space, or a combination of these sites. Intracerebral hemorrhages can occur almost anywhere in the brain, including for example, near the basal ganglia, internal capsule, thalamus, cerebellum, or brain stem. Head trauma is the most common cause of subarachnoid hemorrhage. In a particular embodiment of the invention, the abnormal brain region is a region of brain tissue physiologically affected by stroke.

A disease or condition characterized by abnormal brain tissue may be a neurodegenerative disease. Neurodegenerative diseases or conditions may be characterized by progressive nervous system dysfunction in which neurons in particular structures or regions of the brain deteriorate or die over time. Representative, non-limiting degenerative brain diseases include Alzheimer's, cerebellar atrophies, triplet repeat diseases (e.g., Huntington's disease), Parkinson's disease, Niemann-Pick Type C Disease (NP-C), prior disorders (e.g., Creutzfeldt Jakob Disease), olivopontocerebellar degeneration, motor neuron disease, cerebellar degenerations, Amyotrophic Lateral Sclerosis (i.e., Lou Gehrig's Disease), dementia (e.g., dementia with lewy bodies), as well as diseases involving neurological autoimmune disease (e.g., multiple sclerosis). For a review of neurodegenerative diseases, see Williams A. BMJ (2002) 324:1465-1466;

Other diseases or conditions characterized by abnormal brain tissue are brain and/or spinal cord infections. Microbial infections of the CNS may include, but are not limited to, bacterial, fungal, protozoan, virus-like, and viral infections. Infections include both acute and chronic conditions. Exemplary microbial CNS infections can result in a brain abscess, meningitis, encephalitis, vasculitis, or progressive multifocal leukoencephalopathy (PML). Most abscess-forming infections of the CNS are spread by the blood and are related to septicemia and endocarditis, although there may be direct infection that arises from sinus or middle ear/mastoid infection. Bacterial infections of the CNS may include, but are not limited to infection by *Streptococcus pneumonia, Streptococcus pyogenes, Staphylococcus aureu, Staphylococcus epidermidis, Enterobacteriacea, Propionibacterium, Pseudomonoas aeruginosa, Neisseria meningitis, Haemophilus influenzae* or *Listeria moncytogenes*. Fungal infections of the CNS are less common than bacterial infections, but may arise in individuals with Acquired Immune Deficiency Syndrome (AIDS) and in other immunocompromised individuals, such as those undergoing chemotherapy or immunosuppressive therapy. An example of a protozoan infection of the CNS is late-stage neurological trypanosomiasis, or sleeping sickness, which is caused by infection of the CNS by trypanosoma protozoa.

Viral infections of the CNS may include, but are not limited to aseptic meningitis, encephalitis, and progressive multifocal leukoencephalopathy (PML). Acute neurological syndromes associated with viral infection include, for example, acute viral encephalitis, flaccid paralysis, asceptic meningitis, and post infectious encephalomyelitis. Acute viral encephalitis may be caused by for example, herpes simplex virus, cytomegalovirus, varicella, rabies or an arbovirus. Common viral agents of asceptic meningitis include, for example, enteroviruses, mumps virus and lymphocytic choriomeningitis virus. Post infectious encephalomyelitis is a complication of infection with measles, mumps, rubella and primary varicella-zoster virus infection, for example. Guillain-barre syndrome is also an acute neurological syndrome associated with viral infection.

Additional chronic neurological diseases attributable to viral infection include, subacute sclerosing pan encephalitis (caused by persistent measles infection), spongiform encephalopathies (prion diseases) (e.g., Creutzfeldt-Jakob disease (CJD), Gerstmann-Streussler Syndrome), and retroviral diseases (e.g., HIV-1 and HIV-2) characterized by paralysis, wasting, and ataxia.

Examples of viruses that may cause infections in the CNS, include, but are not limited to, polyomavirus (JCV), which can cause PML; Herpes simplex, which can cause viral encephalitis, and human immunodeficiency virus (HIV) and cytomegalovirus (CMV), each of which can cause white matter encephalitis.

Additional neurological diseases and/or conditions that can be treated according to the present invention include metabolic disorders, including, for example, Abetalipoproteinemi, Central pontine myelinolysis, Galactosemia, Gaucher, Homocystinuria, Kernicterus, Leigh's Disease, Lesch-Nyhan Syndrome, Menkes' Syndrome, Niemann-Pick Type C disease, Reye's Syndrome, Korsakoffs disease, Tay-Sach's disease.

Other neurological diseases and/or conditions that can be treated according to the present invention include, for example, Batten Disease, Canavan disease, Charcot-Marie-Tooth disorder (CMT), dystonia, Neurofibromatosis (NF), Tuberous sclerosis complex (TSC), Aicardi Syndrome; Akinetic Mutism; Amblyopia; Bardet-Biedl Syndrome; cerebral abscess; cerebral edema; Corticobasal Degeneration; Familial Mediterranean Fever; Glycogen Storage Disease Type II; Hallervorden-Spatz Syndrome; intracranial hypertension; intracranial hypotension; Joubert Syndrome; Kluver-Bucy Syndrome; Laurence-Moon Syndrome; Lowe Syndrome; Machado-Joseph; Miller Fisher Syndrome; Moyamoya; olivopontocerebellar atrophy; phenylketonuria; Schizencephaly; transient global amnesia; and Zellweger Syndrome.

In some embodiments the stabilized RAP variants or stabilized RAP variants conjugates of the invention can be used to treat cancer. Non-limiting examples of stabilized RAP variant conjugates includes stabilized RAP variants that are conjugated to a therapeutic polypeptide with anti-cancer activity, including antibody reagents. Antibody reagents for cancer treatment are known in the art and include herceptin, remecade and others. Non-limiting examples of stabilized RAP variant conjugates includes stabilized RAP variants that are conjugated to a therapeutic compound with anti-cancer activity, including chemotherapeutic reagents. Chemotherapeutic reagents include methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Ince/VX-710, VX-853, ZD0101, IS1641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2' deoxycoformycin), Semustine (methyl-CCNU), Teniposide (VM-26) and Vindesine sulfate, but are not so limited.

Furthermore, the stabilized RAP variants and stabilized RAP variant conjugates may also be administered in conjunction with any anti-cancer therapy. Anti-cancer therapies include cancer medicaments, radiation and surgical procedures. As used herein, a "cancer medicament" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

The cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vacine, TA-HPV, TA-CIN, DISC-virus and ImmuCyst/TheraCys, but it is not so limited.

"Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

A metastasis is a region of cancer cells, distinct from the primary tumor location resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Cancer, as used herein, includes the following types of cancer, breast cancer, biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chromic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will be known to one of ordinary skill in the art.

In some embodiments the stabilized RAP variants of the invention can be used to treat bone disorders. Bone disorders include osteoporosis, Paget's disease, osteoarthritis, rheumatoid arthritis, achondroplasia, osteochodrytis, hyperparathyroidism, osteogenesis imperfecta, congenital hypophosphatasia, fribromatous lesions, fibrous displasia, multiple myeloma, abnormal bone turnover, osteolytic bone disease and periodontal disease. Bone remodelling disorders includes metabolic bone diseases which are characterised by disturbances in the organic matrix, bone mineralization, bone remodelling, endocrine, nutritional and other factors which regulate skeletal and mineral homeostasis. Such disorders may be hereditary or acquired and generally are systemic affecting the entire skeletal system.

The stabilized RAP variants of the invention can be generated through biological methods or through chemical synthesis methods. Chemical synthesis method are known in the art and include Fmoc and tBoc based solid state synthesis. Biological synthesis of the stabilized RAP variants of the invention can be achieved through the expression of nucleic acids encoding the stabilized RAP variants.

In another set of embodiments isolated nucleic acids encoding the stabilized RAP variants are presented. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. In order that the coding sequences be translated into a functional protein the coding sequences are operably joined to regulatory sequences. Two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Promoters may be constitutive or inducible. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, the term "stringent conditions" refers to parameters known to those skilled in the art. One example of stringent conditions is hybridization at 65° C. in hybridization buffer (3.5×SSC, 0.02% Ficoll, 0.02% polyvinyl pyrolidone, 0.02% bovine serum albumin (BSA), 25 mM $NaH_2PO_4$ (pH7), 0.5% SDS, 2 mM EDTA). SSC is 0.15M sodium chloride/0.15M sodium citrate, pH7; SDS is sodium dodecylsulphate; and EDTA is ethylene diamine tetra acetic acid. There are other conditions, reagents, and so forth which can be used, which result in the same degree of stringency. A skilled artisan will be familiar with such conditions, and thus they are not given here. The skilled artisan also is familiar with the methodology for screening cells for expression of such molecules, which then are routinely isolated, followed by isolation of the pertinent nucleic acid. Thus, homologs and alleles of the stabilized RAP variants of the invention, as well as nucleic acids encoding the same, may be obtained routinely, and the invention is not intended to be limited to the specific sequences disclosed.

For prokaryotic systems, plasmid vectors that contain replication sites and control sequences derived from a species compatible with the host may be used. Examples of suitable plasmid vectors include pBR322, pUC18, pUC19 and the like; suitable phage or bacteriophage vectors include λgt10, λgt11 and the like; and suitable virus vectors include pMAM-neo, pKRC and the like. Preferably, the selected vector of the present invention has the capacity to autonomously replicate in the selected host cell. Useful prokaryotic hosts include bacteria such as E. coli, Flavobacterium heparinum, Bacillus, Streptomyces, Pseudomonas, Salmonella, Serratia, and the like.

To express the stabilized RAP variants of the invention in a prokaryotic cell, it is necessary to operably join the nucleic acid sequences of the monomers and the linker to a functional prokaryotic promoter. Such promoter may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of E. coli, the α-amylase (Ulmanen et al. 1985, J. Bacteriol. 162, 176-182) and the ζ-28-specific promoters of B. subtilis (Gilman et al. 1984 Gene sequence 32, 11-20), the promoters of the bacteriophages of Bacillus (Gryczan, 1982, in: The Molecular Biology of the Bacilli, Academic Press, Inc., NY), and Streptomyces promoters (Ward et al. 1986, Mol. Gen. Genet. 203, 468-478).

Prokaryotic promoters are reviewed by Glick (1987, J. Ind. Microbiol. 1, 277-282); Cenatiempo (1986, Biochimie 68, 505-516); and Gottesman (1984, Ann. Rev. Genet. 18, 415-442).

Proper expression in a prokaryotic cell also requires the presence of a ribosome binding site upstream of the encoding sequence. Such ribosome binding sites are disclosed, for example, by Gold et al. (1981, Ann. Rev. Microbiol. 35, 365-404).

In some embodiments expression of the stabilized RAP variants of the invention by eukaryotic hosts is preferred. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO or CHO-K1, or cells of lymphoid origin, such as the hybridoma SP2/0-AG14 or the myeloma P3x63Sg8, and their derivatives. Preferred mammalian host cells include SP2/0 and J558L, as well as neuroblastoma cell lines such as IMR 332 that may provide better capacities for correct post-translational processing. Embryonic cells and mature cells of a transplantable organ also are useful according to some aspects of the invention.

In addition, plant cells are also available as hosts, and control sequences compatible with plant cells are available, such as the nopaline synthase promoter and polyadenylation signal sequences.

Another preferred host is an insect cell, for example in Drosophila larvae. When using insect cells as hosts, the Drosophila alcohol dehydrogenase promoter can be used (Rubin, 1988, Science 240, 1453-1459). Alternatively, baculovirus vectors can be engineered to express large amounts of the stabilized RAP variants of the invention in insects cells (Jasny, 1987, Science 238, 1653; Miller et al., 1986 in: Genetic Engineering, Setlow, J. K., et al., eds., Plenum, Vol. 8, pp. 277-297).

Any of a series of yeast gene sequence expression systems which incorporate promoter and termination elements from the genes coding for glycolytic enzymes and which are produced in large quantities when the yeast are grown in media rich in glucose may also be utilized. Known glycolytic gene sequences can also provide very efficient transcriptional control signals. Yeast provide substantial advantages in that they can also carry out post-translational peptide modifications. A number of recombinant DNA strategies exist which utilize strong promoter sequences and high copy number plasmids which can be utilized for production of the desired proteins in yeast. Yeast recognize leader sequences on cloned mammalian gene sequence products and secrete peptides bearing leader sequences (e.g., pre-peptides).

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or which are subject to chemical (such as metabolite) regulation.

As discussed above, expression of the stabilized RAP variants of the invention in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al. 1982, J. Mol. Appl. Gen. 1, 273-288); the TK promoter of Herpes virus (McKnight, 1982 Cell 31, 355-365); the SV40 early promoter (Benoist et al. 1981 Nature (London) 290, 304-310); the yeast gal4 gene sequence promoter (Johnston et al., 1982, Proc. Natl. Acad. Sci. (USA) 79, 6971-6975; Silver et al., 1984, Proc. Natl. Acad. Sci. (USA) 81, 5951-5955).

As is widely known, translation of eukaryotic mRNA is initiated at the codon which encodes the first methionine. For this reason, it is preferable to ensure that the linkage between a eukaryotic promoter and the DNA sequences which encode t stabilized RAP variants of the invention does not contain any intervening codons which are capable of encoding a methionine (i.e., AUG). The presence of such codons results either in the formation of a fusion protein (if the AUG codon is in the same reading frame as the stabilized RAP variants domain coding sequence) or a frame-shift mutation (if the AUG codon is not in the same reading frame as the stabilized RAP variants coding sequence).

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may, for example, provide for prototrophy to an auxotrophic host or may confer biocide resistance to, e.g., antibiotics, heavy metals, or the like. The selectable marker gene sequence can either be directly linked to the DNA gene sequences to be expressed or introduced into the same cell by co-transfection. Additional elements may also be needed for optimal synthesis of the stabilized RAP variants mRNA. These elements may include splice signals, as well as transcription promoters, enhancers, and termination signals.

cDNA expression vectors incorporating such elements include those described by Okayama (1983, Molec. Cell. Biol. 3, 280).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include the following: the ease with which recipient cells that contain the vector may be recognized and selected from those recipient cells which do not contain the vector, the number of copies of the vector which are desired in a particular host and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, and πVX. Such plasmids are, for example, disclosed by Sambrook, et al. (1989, Molecular Cloning: A Laboratory Manual, second edition, edited by Sambrook, Fritsch, & Maniatis, Cold Spring Harbor Laboratory). *Bacillus* plasmids include pC194, pC221, pT127 and the like. Such plasmids are disclosed by Gryczan (1982, in: The Molecular Biology of the Bacilli, Academic Press, NY, pp. 307-329). Suitable *Streptomyces* plasmids include pIJ101 (Kendall et al. 1987, J. Bacteriol. 169, 4177-4183), and *streptomyces* bacteriophages such as φC31 (1986, Chater et al., In: Sixth International Symposium on Actinomycetales Biology, Akademiai Kaido, Budapest, Hungary, pp. 45-54). *Pseudomonas* plasmids are reviewed by John et al. (1986, Rev. Infect. Dis. 8, 693-704), and Izaki (1978, Jpn. J. Bacteriol. 33, 729-742).

Preferred eukaryotic plasmids include, for example, BPV, EBV, SV40, 2-micron circle, and the like, or their derivatives. Such plasmids are well known in the art (1982, Botstein et al., Miami Wntr. Symp. 19, 265-274); Broach, 1981, in: The Molecular Biology of the Yeast *Saccharomyces*: Life Cycle and Inheritance, Cold Spring Harbor Laboratory, Cold Spring Harbor, N.Y., p. 445-470; Broach, 1982, Cell 28:203-204; Bollon et al. 1980, J. Clin. Hematol. Oncol. 10:39-48; Maniatis, 1980, in: Cell Biology: A Comprehensive Treatise, Vol. 3, Gene Sequence Expression, Academic Press, NY, pp. 563-608). Other preferred eukaryotic vectors are viral vectors. For example, and not by way of limitation, the pox virus, herpes virus, adenovirus and various retroviruses may be employed. The viral vectors may include either DNA or RNA viruses to cause expression of the insert DNA or insert RNA. Additionally, DNA or RNA encoding the stabilized RAP variants may be directly injected into cells or may be impelled through cell membranes after being adhered to microparticles.

Once the vector or DNA sequence containing the construct(s) has been prepared for expression, the DNA construct(s) may be introduced into an appropriate host cell by any of a variety of suitable means, i.e., transformation, transfection, conjugation, protoplast fusion, electroporation, calcium phosphate-precipitation, direct microinjection, and the like. After the introduction of the vector, recipient cells are grown in a selective medium, which selects for the growth of vector-containing cells. Expression of the cloned gene sequence(s) results in the production of the stabilized RAP variants. This can take place in the transformed cells as such, or following the induction of these cells to differentiate (for example, by administration of bromodeoxyuracil to neuroblastoma cells or the like).

Conjugates of stabilized RAP variants can be generated to methods known in the art. Therapeutic compounds can be conjugated to the stabilized RAP variants using standard medicinal chemistry. In some embodiments the therapeutic compounds are conjugated to the N-terminal of the stabilized RAP variants. In some embodiments the therapeutic compounds are conjugated to the C-terminal of the stabilized RAP variants. In some embodiments the therapeutic compounds are conjugated to an amino acid side chain of the stabilized RAP variants.

Therapeutic compounds are known in the art and include any compound that can be used to treat a specific disorder. For instance an antiviral compound can be conjugate to the stabilized RAP variant, which can subsequently be used to treat a viral infection, for instance in the brain.

Conjugates of stabilized RAP variants can be generated to methods known in the art. Therapeutic polypeptides can be conjugated to the stabilized RAP variants using standard molecular biology or chemical methods. In some embodiments the therapeutic compounds are conjugated to the N-terminal of the stabilized RAP variants. In some embodiments the therapeutic compounds are conjugated to the C-terminal of the stabilized RAP variants. In some embodiments the therapeutic compounds are conjugated to an amino acid side chain of the stabilized RAP variants. In some embodiments a fusion protein of the stabilized RAP variant and the therapeutic polypeptide is created by linking the nucleic acid encoding the stabilized RAP variant and nucleic acid encoding the therapeutic polypeptide, which can subsequently be expressed as a fusion protein. Therapeutic polypeptides are known in the art and include antibodies, hormones, enzymes etc, or any combination thereof.

The stabilized RAP variants and stabilized RAP conjugates of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the stabilized RAP variants can be administered to a subject by any mode that delivers the stabilized RAP variants to the desired surface. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, and rectal.

For oral administration, the compounds (e.g., stabilized RAP variants, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the stabilized RAP variants (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the stabilized RAP variants (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the stabilized RAP variants or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the stabilized RAP variants (or derivatives thereof). The stabilized RAP variants is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of stabilized RAP variants (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified stabilized RAP variants may also be prepared in different formulations depending on the type of chemical modification or the type of device employed.

Formulations suitable for use with a nebulizer, either jet or ultrasonic, will typically comprise stabilized RAP variants (or derivative) dissolved in water at a concentration of about 0.1 to 25 mg of biologically active stabilized RAP variants per mL of solution. The formulation may also include a buffer and a simple sugar (e.g., for stabilized RAP variants stabilization and regulation of osmotic pressure). The nebulizer formulation may also contain a surfactant, to reduce or prevent surface induced aggregation of the stabilized RAP variants caused by atomization of the solution in forming the aerosol.

Formulations for use with a metered-dose inhaler device will generally comprise a finely divided powder containing the stabilized RAP variants (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing stabilized RAP variants (or derivative) and may also include a bulking agent, such as lactose, sorbitol, sucrose, or mannitol in amounts which facilitate dispersal of the powder from the device, e.g., 50 to 90% by weight of the formulation. The stabilized RAP variants (or derivative) should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds' to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, 1990, Science 249, 1527-1533, which is incorporated herein by reference.

The stabilized RAP variants and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a stabilized RAP variants and optionally therapeutic agents included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the, may be provided in particles. Particles as used herein means nano or microparticles (or in some instances larger) which can consist in whole or in part of the stabilized RAP variants or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the stabilized RAP variants in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by Sawhney et. al., 1993, Macromolecules 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

The stabilized RAP variants of the invention are useful in effective amounts. It should be appreciated that effective amounts relate both to stabilized RAP variants and conjugates of RAP variants. The term effective amount refers to the amount necessary or sufficient to realize a desired biologic effect. Examples of biological effects include 1) increased transport of a compound conjugated to a stabilized RAP variant and 2) increased antagonist or agonist effect or a combination thereof. The increase may be 10%, 20%, 30%, 40%, 50% . . . 2 fold . . . 5 fold or more. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the particular stabilized RAP variants being administered, the size of the subject, or the severity of the disease or condition. One of ordinary skill in the art can empirically determine the effective amount of a particular stabilized RAP variants or antibody and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate system levels can be determined by, for example, measurement of the patient's peak or sustained plasma level of the drug. "Dose" and "dosage" are used interchangeably herein.

Generally, daily oral doses of active compounds will be from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from an order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

EXAMPLES

The LDL receptor type-A (LA) repeats constitute the RAP-binding sites on LRP1 and related proteins of the LDL receptor family of proteins (LDLRFP). Biochemical studies have shown that each of the three domains of RAP can independently bind to two-repeat fragments of LRP1, with D3 binding with higher affinity than either domains one (D1) or two (D2) in isolation. In the complex between RAP-D3 and the LA3-4 repeat pair from the LDLR, D3 contacts the receptor fragment at two docking sites, one per module. The structural binding paradigm revealed by this complex represents a general mode for binding of RAP-D3 to proteins of the LDLRFP. The interface at each docking site is dominated by electrostatic interactions between conserved acidic residues on the LA module and a lysine residue projecting from helix 2 of the RAP helical bundle, with the mode of recognition nearly identical at the two sites. The LA repeats are found in clusters on the receptors, and like the three domains of RAP, are typically connected by flexible linkers, suggesting that the full-length proteins bind tightly to each other in part as a result of avidity effects.

Figure 2:
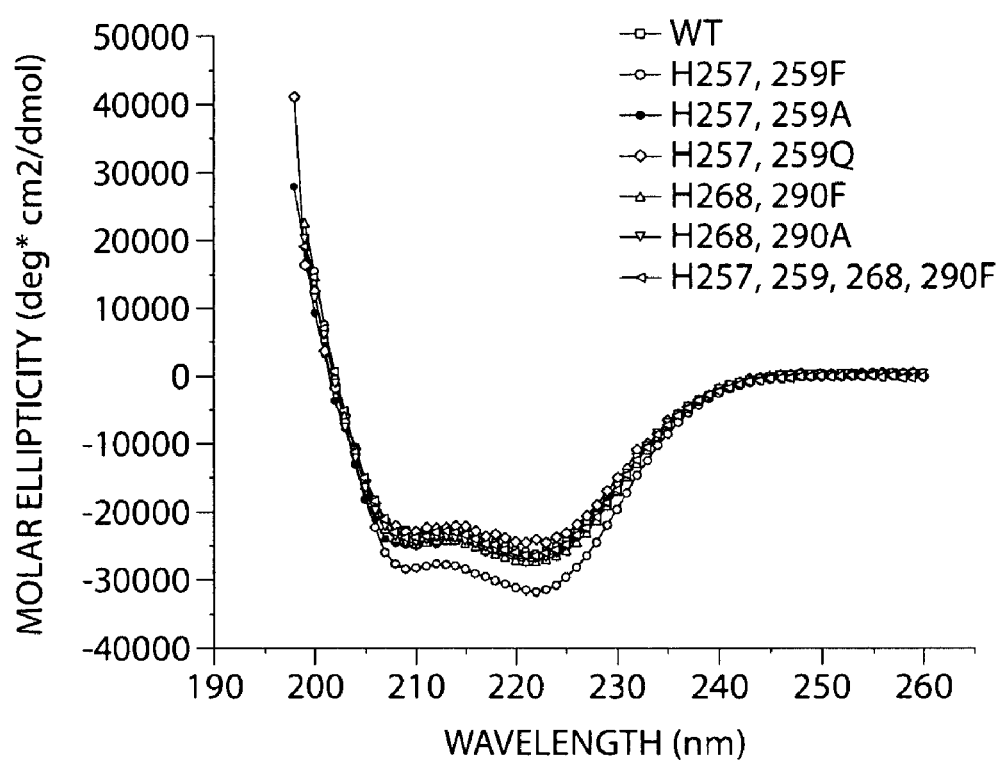
FIG. 2 depicts the far-UV CD spectra of RAP-D3 WT and mutants. RAP-D3 mutants are as helical as wild-type.

At neutral pH, wild-type RAP-D3 is highly helical (FIG. 2A), undergoes a cooperative thermal unfolding transition at 42° C. (FIG. 2B), and a pH-induced unfolding transition at a pH of 6.3 (FIG. 2C). We constructed variants of the RAP-D3 helical bundle that were thermostable, retained near-native affinity for LA repeat pairs, and exhibited increased resistance to unfolding induced by low pH.

Stabilized forms of RAP-D3 were created by replacing histidine residues at or near the interface between helices two and three of the RAP-D3 helical bundle: H257, H259, H268, and H290 (FIG. 1). We created mutated forms of RAP-D3 in which either two or four of these histidines were replaced by alanines, glutamines, or phenylalanines (See below), three different non-titratable amino acids, in order to create a form of RAP-D3 resistant to low-pH induced unfolding.

First, we replaced pairs of histidines with alanines or glutamines to create the H257A/H259A, H257Q/H259Q, and H268A/H290A mutants of RAP-D3. Each RAP-D3 exhibits essentially the same helical content as the wild-type protein at 4° C. (FIG. 2A), as judged by circular dichroism spectroscopy (CD). However, the $T_m$ values for the H257A/H259A and H257Q/H259Q mutants are 36.7 and 35.7° C., respectively (FIG. 2B), indicating that each protein would be at least 50% unfolded at physiologic temperature and therefore not a stabilized RAP variant. The other alanine variant, H268A/H290A exhibits a melting temperature ($T_m$) and low-pH induced unfolding transition indistinguishable from those of wild-type RAP-D3, making it also unsuitable as a stabilized RAP variant.

We next substituted the histidine residues with phenylalanine, which is non-titratable, hydrophobic, and nearly isosteric to histidine. In all, three proteins were created, H257F/H259F and H268F/H290F, and a four-site mutant H257F/H259F/H268F/H290F (RAP-D3-quad). Each of these phenylalanine variants is as helical as the wild-type protein, as judged by CD (FIG. 2A). Unlike the alanine and glutamine mutants, however, all three phenylalanine variants are more resistant to thermal denaturation and to low pH-induced unfolding, with the RAP-D3 being the most resistant to both acid and heat (FIGS. 2B, C). The $T_m$ values for the three proteins range from 49.3 (H268F/H290F) to 57.6° C. (RAP-D3-quad), and the midpoints for low pH-induced unfolding range from pH 5.6 (H257F/H259F) to pH 4.8 (RAP-D3-quad).

We next confirmed that the acid- and heat-resistant forms of RAP-D3 still bound to a polypeptide consisting of the LA3-4 module pair of the LDLR, by measuring the binding affinity of each RAP protein for LA3-4 by isothermal titration calorimetry (ITC) at neutral pH (FIG. 3 and Table 1). The stoichiometry of binding for all proteins tested is 1:1, as predicted from the X-ray structure of the complex between wild-type RAP-D3 and LA3-4, and the affinities of the mutant proteins are within a factor of two when compared with wild-type RAP-D3. At low salt concentrations (50 mM NaCl), the measured dissociation constant for LA3-4 with wild-type RAP-D3 is 480±40 nM, a value that rises to 1.2±0.1 microM at a NaCl concentration of 150 mM. For the three phenylalanine mutants of RAP-D3, the affinities are 850±160 nM (H257F/H259F; 50 mM NaCl), 1.2±0.3 nM (H269F/H290F; 50 mM NaCl), and 850±160 nM (RAP_D3-quad; a NaCl concentration of 100 mM was needed for this titration for technical reasons).

We examined whether the sensitivity of the different forms of RAP-D3 to pH-induced unfolding correlated with the sensitivity of RAP-D3: LA3-4 complexes to low pH-induced dissociation, as judged using a size exclusion chromatography assay (FIG. 4). For wild-type RAP-D3, complexes exhibit evidence of dissociation by pH 6.0, and dissociation is nearly complete by pH 5.5 (FIG. 9). In contrast, complexes formed with the H257F/H258F form of RAP do not exhibit evidence of dissociation until pH 5.0, and complexes with RAP_D3-quad do not undergo dissociation even at pH 5.0. The dissociation data correlate tightly with the pH-induced unfolding studies of the different RAP-D3 proteins, supporting a model in which dissociation of complexes is normally driven by unfolding of the helical bundle at the mildly acidic pH of the Golgi (pH 6.3).

Since low-pH induced dissociation of RAP:LRP-1 complexes is functionally important in cells, a RAP mutant with the H257F/H259F/H268F/H290F substitutions (RAP-quad) would remain bound to LRP at the pH of the Golgi, and interfere with transport of LRP to the cell surface in a dominant negative fashion. Therefore, we compared the endogenous LRP-1 reaching the cell surface in HepG2 cells transfected with either wild-type RAP or the full length RAP-quad mutant (FIG. 5). Transfection of RAP into HepG2 cells does not have a detectable the amount of endogenous LRP at the cell surface in this assay when compared with vector alone (FIG. 5). In contrast, transfection with RAP-quad results in a dramatic reduction in cell surface LRP-1 levels, as predicted by the pH-induced unfolding model.

The RAP-D3 variants are resistant to thermal and low-pH induced denaturation (FIGS. 3,4). They form stable complexes with a two-repeat fragment of the LDL receptor (Table 1), and complexes of this fragment with the mutated forms of RAP-D3 are insensitive to pH-induced dissociation (FIG. 6). The same substitutions introduced into full-length RAP result in tight binding of RAP to LRP-1 in cells, and interfere with LRP-1 export in cell-based assays (FIG. 7).

RAP and RAP-D3 Constructs (Official Gene Symbol LRPAP1)

| From Genbank: |
| --- |
| LOCUS HUMA2MGRAP 1493 bp mRNA<br>linear<br>PRI 30-OCT-1994<br>DEFINITION Human alpha-2-macroglobulin receptor-associated protein mRNA, complete cds.<br>ACCESSION M63959 |

Each of these four recombinant polypeptides was expressed as a Glutathione S-transferase fusion protein, modified to contain a tobacco etch virus cleavage site (ENLYFQ), so that enzymatic cleavage released the target protein with an additional N-terminal glycine residue:

1. RAP-D3 [H257F/H259F], which consists of residues 216-323 of the mature RAP protein with the H257F and H259F substitutions, as follows:

```
                                       (SEQ ID NO.: 1)
. . . glutathione-S-transferase . . .
ENLYFQGAEFEEPRVIDL

WDLAQSANLT DKELEAFREE LKHFEAKIEK FNFYQKQLEI

AHEKLRHAES VGDGERVSRS REKHALLEGR TKELGYTVKK

HLQDLSGRIS RARHNEL
```

2. RAP-D3 [H268F/H290F], which consists of residues 216-323 of the mature RAP protein with the H268F and H290F substitutions, as follows:

```
                                         (SEQ ID NO.: 2)
 . . . glutathione-S-transferase . . .
ENLYFQGAEFEEPRVIDL

WDLAQSANLT DKELEAFREE LKHFEAKIEK HNHYQKQLEI

AFEKLRHAES VGDGERVSRS REKFALLEGR TKELGYTVKK

HLQDLSGRIS RARHNEL
```

3. RAP-D3-quad: which consists of residues 216-323 of the mature RAP protein with the H257F, H259F, H268F, and H290F substitutions, as follows:

```
                                         (SEQ ID NO.: 3)
 . . . glutathione-S-transferase . . .
ENLYFQGAEFEEPRVIDL

WDLAQSANLT DKELEAFREE LKHFEAKIEK FNFYQKQLEI

AFEKLRHAES VGDGERVSRS REKFALLEGR TKELGYTVKK

HLQDLSGRIS RARHNEL
```

4. RAP-quad, which consists of residues 1-323 of the mature RAP protein with H257F, H259F, H268F, and H290F substitutions, as follows:

```
                                         (SEQ ID NO.: 4)
 . . . glutathione-S-transferase . . .
ENLYFQGYSREKNQPKPSPKRES

GEEFRMEKLN QLWEKAQRLH LPPVRLAELH ADLKIQERDE

LAWKKLKLDG LDEDGEKEAR LIRNLNVILA KYGLDGKKDA

RQVTSNSLSG TQEDGLDDPR LEKLWHKAKT SGKFSGEELD

KLWREFLHHK EKVHEYNVLL ETLSRTEEIH ENVISPSDLS

DIKGSVLHSR HTELKEKLRS INQGLDRLRR VSHQGYSTEA

EFEEPRVIDL WDLAQSANLT DKELEAFREE LKHFEAKIEK

FNFYQKQLEI AFEKLRHAES VGDGERVSRS REKFALLEGR

TKELGYTVKK HLQDLSGRIS RARHNEL
```

(residues 216-323) was cloned into the donor vector, pDONR201 (Gateway Cloning System, Invitrogen, Carlsbad, Calif.), and then into the expression vector, pDEST15 for expression as a GST-fusion protein with an N-terminal tobacco etch virus (TEV) protease cleavage site (ENLTFQG). Mutations in RAP-D3 were introduced via site-directed mutagenesis with a Quickchange mutagenesis kit (Stratagene, La Jolla, Calif.) and were verified by DNA sequencing.

Expression of RAP-D3 variants was induced by the addition of 0.5 mM IPTG during log phase growth ($A_{595}$=0.6-0.8) in BL21(DE3) cells. Bacteria were harvested by centrifugation and lysed by probe sonication in lysis buffer (50 mM Tris pH 8.0, 150 mM NaCl, 20% (w/v) sucrose, and 1 mM EDTA). Cell debris was removed by centrifugation and the soluble GST-{TEV site}-RAP-D3 variant in the supernatant was captured on Glutathione Sepharose 4B beads (GE Healthcare Biosciences Corp., Piscataway, N.J.). After two washes with TBS (Tris-buffered saline; 150 mM NaCl, 20 mM Tris, pH 8.0), the fusion protein was cleaved with TEV protease (6×His-tagged) in TBS supplemented with 0.5 mM EDTA and 1 mM DTT for 1 h at 20° C. and then overnight at 4° C. to release the desired RAP-D3 variant from the beads. The TEV protease was then removed from the solution by capture onto Ni-NTA beads (Qiagen, Hilden, Germany) followed by filtration through fitted glass. Monomeric RAP-D3 was subsequently isolated via size-exclusion chromatography on a Superdex-S75 column (Pharmacia, Piscataway, N.J.).

Circular Dichroism (CD).

CD scans were acquired on an AVIV 62DS spectropolarimeter, equipped with a Peltier effect temperature controller. All protein samples (~1.5 μM) were dialyzed against 10 mM NaP pH 7.3, 100 mM NaCl. Scans were conducted at 4° C. and were acquired from 196 to 260 nm, with a bandwidth of 1.5 nm, a scan step of 1 nm, an averaging time of 3 s, and three repeats per scan in a 1 cm path length cuvette. For thermal denaturation experiments, the temperature dependence of the molar ellipticity was followed at 222 nm, where the temperature was raised 1° C./min, using a bandwidth of 1.5 nm, an averaging time of 30 s, and an equilibration time of 2 min. For pH stability studies, the pH was altered by diluting a stock into a buffer of defined pH and then adjusting the pH to the desired value with 0.1 M HCl or NaOH, if needed. CD collection conditions were as described for thermal denaturation studies.

Isothermal Titration Calorimetry (ITC).

RAP-D3 titrations were performed in 20 mM HEPES, pH 7.3, 50-150 mM NaCl, 5 mM $CaCl_2$ at 25° C. using a VP-ITC calorimeter (MicroCal Inc., Northampton, Mass.) in a 1.3 mL reaction vessel. A RAP-D3 stock solution (132-178 μM) was added in 6-8 μL increments to LA3-4 (20-25 μM). Calorim-

TABLE 1

Thermodynamic parameters derived from the microcalorimetric titration of LA3-4 with RAPD3 protein variants

| Ligand | N | ΔH (kcal/mol·K) | K | $K_D$ (= 1/K) (μM) | [NaCl] (mM) |
|---|---|---|---|---|---|
| RAPD3_WT | 0.89 ± 0.01 | −9.1 ± 0.1 | 2.1E06 ± 1.8E05 | 0.48 ± 0.04 | 50 |
| RAPD3_WT | 0.85 ± 0.01 | −6.8 ± 0.1 | 8.6E05 ± 6.2E04 | 1.17 ± 0.08 | 150 |
| RAPD3_H257, 259F | 0.89 ± 0.02 | −8.6 ± 0.2 | 1.2E06 ± 2.2E05 | 0.85 ± 0.16 | 50 |
| RAPD3_H268, 290F | 0.98 ± 0.02 | −9.3 ± 0.3 | 8.6E05 ± 2.0E05 | 1.16 ± 0.27 | 50 |
| RAPD3_Quad* | 0.89 ± 0.02 | −5.4 ± 0.2 | 1.2E06 ± 2.2E05 | 0.85 ± 0.16 | 100 |

N = number of binding sites
*Quad = RAPD3_H257, 259, 268, 290F
Estimate of run-to-run error ~26%

Protein Expression and Purification.

The LA3-4 module pair was expressed as described previously (Fisher et al. 2006 Mol. Cell. 22:277-283). RAP-D3 etry data were fitted to a single-site binding model using the program Origin 5.0 (OriginLab Corp., Northampton, Mass.).

Gel Filtration Studies.

Equimolar quantities of RAP-D3 and LA3-4 (143 μM) were incubated for one hour at 4° C. in 10 mM HEPES containing 100 mM NaCl and 2.5 mM $CaCl_2$ at pH 7.3. Equivalent amounts of each individual protein were comparably incubated. Aliquots of formed complexes were then transferred to buffer with pH ranging from 7.3 to 5.0. pH was adjusted to their final value using 0.1 M NaOH or HCl. Samples were subsequently incubated at 4° C., 1 hr. For each complex, 200 μl was injected onto a pre-equilibrated Superdex 75 HiLoad 16/60 gel filtration column (Pharmacia) on an FPLC system with a UV-2 detector at 25° C., 0.8 ml/min.

Cell Surface LRP-1 Expression Analysis by FACS.

HepG2 cells (kind gift of Chinweike Ukomadu) cultured in EMEM (Eagle's Minimum Essential Medium (American Type Culture Collection) supplemented with 10% fetal bovine serum (Cambrex, East Rutherford, N.J.) and 100 U penicillin/ml (Invitrogen) and 100 μg streptomycin/ml (Invitrogen) were split into 10 cm dishes at a confluency of 33%. When cells were 90% confluent, they were transfected using Lipofectamine 2000 reagent (Invitrogen) with 10 μg each of plasmids expressing GFP and empty vector, wild-type full-length RAP or full-length RAP harboring the H257,259,268, 290F mutations (Quad H:F). All plasmids were of the pcDNA5/FRT/TO backbone (Invitrogen). For the RAP variants, the constructs were built to include the RAP signal peptide plus four amino acids (YSRE) followed by a hemagglutinin (HA) tag upstream of the insert.

Twenty-four hours post-transfection, each 10 cm dish of transfected cells was split into 10 cm dishes at 50% confluency. This procedure yields three groups of cells, 2 dishes per group: a mock-treated pool and two pools of cells treated with wild-type full-length RAP or full-length RAP Quad H:F, respectively.

Forty-eight hours post-transfection, cells were harvested by detaching them from each dish with warm EMEM and were then transferred into an Eppendorf tube. Cells were washed with ice-cold PBS. Cells for analysis of cell-surface expression of endogenous LRP-1 were pelleted at 2000 rpm for 3 min using a table-top microfuge and then resuspended in 500 μL of primary anti-LRP-1 antibody solution and incubated on a rotator at 4° C. for 30 min. Cells were then recovered by centrifugation, washed once in PBS, and resuspended in 500 μL of APC-conjugated secondary antibody solution and incubated on a rotator in the dark at 4° C. for 30 min. Primary antibody solution was a monoclonal mouse anti-LRP-1 antibody (Abcam, Cambridge, Mass.) diluted 1:250 in PBS with 0.1% sodium azide. Secondary antibody solution was an APC-conjugated goat anti-mouse antibody (Molecular Probes, Carlsbad, Calif.) diluted 1:100 in PBS with 0.1% sodium azide. Cells for analysis of total expression of LRP-1 were fixed and semi-permeabilized (BD Cytofix/Cytoperm, BD Biosciences, Rockville, Mass.) and then blocked with 10% goat serum (Jackson ImmunoResearch, West Grove, Pa.) prior to incubation with primary antibody solution.

Flow cytometric analysis, pelleted cells were washed in ice-cold PBS, transferred into 5 mL culture tubes (Falcon 2093) and placed on ice. To restrict analysis to live, transfected cells, a double gating strategy was set up as follows: Scattering properties were used to gate on live cells, followed by careful selection of GFP-positive cells to enrich for cells transfected with RAP. Using 5000 cells, a histogram plot was generated for each experimental condition. All data were acquired on a FACScalibur apparatus (BD Biosciences) and analyzed using the CellQuest Pro software (version 5.1.1).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All publications, patents and sequence database entries mentioned herein, including those items listed below, are hereby incorporated by reference in their entirety as if each individual publication or patent was specifically and individually indicated to be incorporated by reference. In case of conflict, the present application, including any definitions herein, will control.

What is claimed is:

1. A composition comprising a domain 3 Receptor Associated Protein (RAP),
wherein one or more of the histidines of the domain is replaced with a hydrophobic residue selected from the group consisting of Phe, Val, Leu, Ile and Trp.

2. The composition of claim 1, wherein the domain 3 RAP is a full-length RAP.

3. The composition of claim 1, wherein the domain 3 RAP is less than a full-length RAP.

4. The composition of claim 3, wherein the domain 3 RAP consists of domain 3 of RAP.

5. The composition of claim 1, wherein at least one of the hydrophobic residues interacts with a protein of the low density lipoprotein receptor family of proteins (LDLRFP), when RAP is bound to the protein of the LDLRFP.

6. The composition of claim 5, wherein the protein of the LDLRFP is low-density lipoprotein receptor-related protein 1 (LRP1).

7. The composition of claim 1, wherein at least one of the histidines is replaced with a phenylalanine.

8. The composition of claim 7, wherein a) His 257, His 259, His 268, or His 290 is replaced by Phe, b) His 257 and His 259 are replaced by Phe, c) His 268 and His 290, are replaced by Phe, or d) His 257, His 259, His 268 and His 290 are replaced by Phe.

9. The composition of claim 1, wherein the domain 3 RAP is conjugated to a therapeutic compound.

10. The composition of claim 1, wherein the domain 3 RAP is fused to a therapeutic polypeptide to produce a fusion peptide.

11. A method for transporting a therapeutic compound into a target cell comprising contacting the target cell with the composition of claim 9.

12. A method for transporting a therapeutic polypeptide into a target cell comprising contacting the target cell with the fusion peptide of claim 10.

13. A method for attenuating activity of a cell expressing one or more proteins of the LDLRFP in a subject comprising administering to a subject an effective amount of a composition of claim 1.

14. The method of claim 13, wherein the protein of the LDLRFP is LRP1.

15. A method for treating a solid tumor in a subject comprising administering to a subject an effective amount of a composition of claim 1 to treat the cancer.

16. A method for treating osteoporosis in a subject comprising administering to a subject an effective amount of a composition of claim 1 to treat the bone disorder.

* * * * *